US012609923B2

(12) United States Patent
Annas et al.

(10) Patent No.: US 12,609,923 B2
(45) Date of Patent: *Apr. 21, 2026

(54) SYSTEMS AND METHODS FOR AUTOMATING PROCESSES FOR REMOTE WORK

(71) Applicant: Eagle Telemedicine, LLC, Atlanta, TX (US)

(72) Inventors: Robert E. Annas, Atlanta, GA (US); Jason Povio, Canton, GA (US); Talbot McCormick, Atlanta, GA (US)

(73) Assignee: Eagle Telemedicine, LLC, Atlanta, GA (US)

( * ) Notice: Subject to any disclaimer, the term of this patent is extended or adjusted under 35 U.S.C. 154(b) by 20 days.

This patent is subject to a terminal disclaimer.

(21) Appl. No.: 18/759,421

(22) Filed: Jun. 28, 2024

(65) Prior Publication Data

US 2024/0356911 A1     Oct. 24, 2024

Related U.S. Application Data

(63) Continuation-in-part of application No. 17/454,464, filed on Nov. 10, 2021, now Pat. No. 12,028,334, (Continued)

(51) Int. Cl.
| | |
|---|---|
| *H04L 9/40* | (2022.01) |
| *G06F 9/451* | (2018.01) |

(Continued)

(52) U.S. Cl.
CPC ............ *H04L 63/083* (2013.01); *G06F 9/451* (2018.02); *G06F 9/547* (2013.01); *G06F 40/40* (2020.01);
(Continued)

(58) Field of Classification Search
CPC ..... H04L 63/083; H04L 63/08; H04L 67/125; G16H 40/67; G16H 10/60; G06F 9/451;
(Continued)

(56) References Cited

U.S. PATENT DOCUMENTS

| | | | |
|---|---|---|---|
| 5,586,260 | A | 12/1996 | Hu |
| 6,006,333 | A | 12/1999 | Nielsen |

(Continued)

FOREIGN PATENT DOCUMENTS

| | | | |
|---|---|---|---|
| CA | 2827454 A1 | 8/2012 | |
| WO | WO 2007114972 A2 | 10/2007 | |
| WO | WO 2021056028 A1 | 7/2023 | |

OTHER PUBLICATIONS

ETHOS (Eagle Telemedicine Operating System) Platform, provided by Eagle Telemedicine LLC, <www.eagletelemedicine.com/telemedicine-technology-enabled-inpatient-care-how-does-eagle-deliver-it-ethos-is-the-key/> dated Apr. 4, 2019, , retrieved from the Internet Archive on Nov. 3, 2021 at <web.archive.org/web/20211103220432/https://www.eagletelemedicine.com/telemedicine-technology-enabled-inpatient-care-how-does-eagle-deliver-it-ethos-is-the-key/>.

(Continued)

*Primary Examiner* — Ayoub Alata
(74) *Attorney, Agent, or Firm* — André J. Bahou; Shoaib Mithani; Bradley Arant Boult Cummings LLP

(57) ABSTRACT

A method may include a method of automating processes for remote work. The method may include receiving, at a server, first login data from a client software application. The client software application may be executing on a user device of a remote worker user. The method may include authenticating the remote worker user based on the first login data. The method may include receiving, at the server, command data from the client software application. The command data may include data indicating to the server to launch a software
(Continued)

1500

Receive, at a server, first login data from a client software application — 1502

Authenticate the remote worker user based on the login data — 1504

Receive selection data, the selection data including an entity identifier — 1506

Retrieve entity data from a database based on the entity identifier — 1508

Send at least a portion of the entity data to a client software application — 1510 application. The method may include launching, on the server, the software application. The method may include inputting, using a robotic process automation (RPA) process, second login data of the remote worker user into the software application. The method may include key site information, speech-to-text functionality, onboarding functionality, automated support, or activity logging.

20 Claims, 21 Drawing Sheets

Related U.S. Application Data which is a continuation of application No. 17/444,659, filed on Aug. 6, 2021, now Pat. No. 12,113,787, which is a continuation of application No. 17/444,658, filed on Aug. 6, 2021, now abandoned, which is a continuation of application No. 17/444,657, filed on Aug. 6, 2021, now abandoned.

(51) Int. Cl.

| | |
|---|---|
| *G06F 9/54* | (2006.01) |
| *G06F 40/40* | (2020.01) |
| *G06N 20/00* | (2019.01) |
| *G10L 15/26* | (2006.01) |
| *G16H 10/60* | (2018.01) |
| *G16H 40/67* | (2018.01) |
| *H04L 67/125* | (2022.01) |

(52) U.S. Cl.
CPC .............. *G06N 20/00* (2019.01); *G10L 15/26* (2013.01); *G16H 10/60* (2018.01); *G16H 40/67* (2018.01); *H04L 63/08* (2013.01); *H04L 67/125* (2013.01)

(58) Field of Classification Search
CPC ......... G06F 40/40; G06F 9/547; G06N 20/00; G10L 15/26
See application file for complete search history.

(56) References Cited

U.S. PATENT DOCUMENTS

| | | | |
|---|---|---|---|
| 6,205,480 | B1 | 3/2001 | Broadhurst et al. |
| 6,934,706 | B1 | 8/2005 | Mancuso et al. |
| 7,039,714 | B1 | 5/2006 | Blakley III et al. |
| 7,899,674 | B1 | 3/2011 | Rubin |
| 8,046,823 | B1 | 10/2011 | Begen et al. |
| 8,332,917 | B2 | 12/2012 | Forster et al. |
| 8,527,774 | B2 | 9/2013 | Fallows et al. |
| 9,787,664 | B1 | 10/2017 | Subbiah et al. |
| 10,891,352 | B1 | 1/2021 | Hane et al. |
| 10,917,400 | B1 | 2/2021 | Goings |
| 11,145,407 | B1 | 10/2021 | Jesneck et al. |
| 11,297,459 | B2 | 4/2022 | Raduchel et al. |
| 2003/0065940 | A1 | 4/2003 | Brezak et al. |
| 2003/0125983 | A1 | 7/2003 | Flack et al. |
| 2003/0195970 | A1 | 10/2003 | Dinh et al. |
| 2004/0088317 | A1 | 5/2004 | Fabrick et al. |
| 2004/0250118 | A1 | 12/2004 | Andreev et al. |
| 2005/0015490 | A1 | 1/2005 | Saare et al. |
| 2006/0075224 | A1 | 4/2006 | Tao |
| 2006/0218630 | A1 | 9/2006 | Pearson et al. |
| 2007/0067465 | A1 | 3/2007 | Blinn et al. |
| 2007/0288268 | A1 | 12/2007 | Weeks |
| 2008/0281629 | A1 | 11/2008 | Scott et al. |
| 2009/0024411 | A1 | 1/2009 | Albro et al. |
| 2010/0024015 | A1 | 1/2010 | Hardt |
| 2010/0146611 | A1 | 6/2010 | Kuzin et al. |

| | | | |
|---|---|---|---|
| 2011/0162046 | A1 | 6/2011 | Forster et al. |
| 2011/0225114 | A1 | 9/2011 | Gotthardt |
| 2011/0282688 | A1 | 11/2011 | Raggousis |
| 2012/0109686 | A1 | 5/2012 | Higbie et al. |
| 2012/0167234 | A1 | 6/2012 | Donfried et al. |
| 2012/0197657 | A1 | 8/2012 | Prodanovic |
| 2013/0218917 | A1 | 8/2013 | Bell |
| 2013/0305338 | A1 | 11/2013 | Casals Andreu |
| 2014/0109205 | A1 | 4/2014 | Lymer et al. |
| 2014/0143554 | A1 | 5/2014 | Torkkel |
| 2014/0344910 | A1 | 11/2014 | Kim et al. |
| 2014/0379374 | A1 | 12/2014 | Vinals |
| 2015/0066536 | A1 | 3/2015 | Spates |
| 2015/0127358 | A1 | 5/2015 | Porter et al. |
| 2015/0143468 | A1 | 5/2015 | Hebert et al. |
| 2015/0310455 | A1 | 10/2015 | Vinals |
| 2015/0356250 | A1 | 12/2015 | Polimeni |
| 2016/0004822 | A1 | 1/2016 | Patil |
| 2016/0063189 | A1 | 3/2016 | Soon-Shiong et al. |
| 2016/0080360 | A1 | 3/2016 | Child et al. |
| 2016/0092642 | A1 | 3/2016 | Maurer et al. |
| 2016/0105413 | A1 | 4/2016 | Yasaki et al. |
| 2016/0205089 | A1 | 7/2016 | Ott et al. |
| 2016/0217261 | A1 | 7/2016 | Tuthill et al. |
| 2016/0239617 | A1 | 8/2016 | Farooq et al. |
| 2016/0283676 | A1 | 9/2016 | Lyon et al. |
| 2016/0314248 | A1 | 10/2016 | Klocek et al. |
| 2016/0357914 | A1 | 12/2016 | Morris et al. |
| 2017/0116373 | A1 | 4/2017 | Ginsburg et al. |
| 2017/0116384 | A1 | 4/2017 | Ghani |
| 2017/0180352 | A1 | 6/2017 | Akbarpour |
| 2017/0195317 | A1 | 7/2017 | Manza et al. |
| 2017/0201588 | A1 | 7/2017 | Schmidt et al. |
| 2018/0004928 | A1 | 1/2018 | Hayashi et al. |
| 2018/0047121 | A1 | 2/2018 | Bhattacharyya |
| 2018/0122500 | A1 | 5/2018 | Harrell Vines |
| 2018/0144814 | A1 | 5/2018 | Bright |
| 2018/0165170 | A1 | 6/2018 | Hegdal et al. |
| 2018/0197143 | A1 | 7/2018 | Daub et al. |
| 2019/0147672 | A1 | 5/2019 | Zwink et al. |
| 2019/0333613 | A1 | 10/2019 | Zaidi et al. |
| 2019/0386980 | A1 | 12/2019 | Kludy |
| 2020/0020453 | A1 | 1/2020 | Yarbray et al. |
| 2020/0051677 | A1 | 2/2020 | Harrison |
| 2020/0092282 | A1 | 3/2020 | Childress et al. |
| 2020/0111548 | A1 | 4/2020 | Ford et al. |
| 2020/0126644 | A1 | 4/2020 | Polzin |
| 2020/0135205 | A1 | 4/2020 | Tan et al. |
| 2020/0176111 | A1 | 6/2020 | Woods |
| 2020/0177386 | A1 | 6/2020 | Mahmood et al. |
| 2020/0227146 | A1 | 7/2020 | Tuman, III |
| 2020/0264860 | A1 | 8/2020 | Srinivasan et al. |
| 2020/0294640 | A1 | 9/2020 | Ginsburg |
| 2020/0321086 | A1 | 10/2020 | Rao et al. |
| 2020/0350072 | A1 | 11/2020 | McEwing et al. |
| 2021/0110919 | A1 | 4/2021 | Garner et al. |
| 2021/0225378 | A1 | 7/2021 | Montemurro et al. |
| 2021/0319895 | A1 | 10/2021 | Joao |
| 2021/0385207 | A1 | 12/2021 | Sridharan et al. |
| 2021/0385224 | A1 | 12/2021 | Singh et al. |
| 2022/0028382 | A1 | 1/2022 | Ganmukhi et al. |
| 2022/0052847 | A1 | 2/2022 | Gonzalez Cervantes et al. |
| 2022/0167922 | A1 | 6/2022 | Gross et al. |
| 2022/0191041 | A1 | 6/2022 | Gerhard et al. |

OTHER PUBLICATIONS

Pengsart, Pagapom et al., "ADFS Authentication for Healthcare System," 2nd International Conference on Information Technology (INCIT), Nakhonpathom, Thailand, Nov. 2-3, 2017, pp. 1-6, doi: 10.1109/INCIT.2017.8257851.

Tulu, Bengisu et al., "Secured Video Conferencing Desktop Client for Telemedicine," Proceedings 5th International Workshop on Enterprise Networking and Computing in Healthcare Industry (HealthCom), Santa Monica, CA, USA, 2003, pp. 61-65.

FIG. 1          PRIOR ART

| Username | Password_Hash | First Name | Last Name | Birthday | Licensed |
|----------|---------------|------------|-----------|----------|----------|
| DrGonzalez | ae46ff1d | Jose | Gonzalez | 1963-05-01 | AL, CA |
| AliceSmith | e336e1a | Alice | Smith | 1971-01-23 | WA |
| RobPorter | 79dce12 | Robert | Porter | 1981-12-07 | CT, NY |
| ManuelH | 6e4f2a1 | Manuel | Hansen | 1975-11-14 | TN, UT, KY |

| Username | Entity | Entity_Username | Entity_Passowrd | Functions |
|----------|--------|-----------------|-----------------|-----------|
| DrGonzalez | Boston Medical Center | DrGonzalez | Password123 | Video, RDT, EMR |
| DrGonzalez | Massachusetts General Hospital | JoseGonz | Password456 | Video, RDT |
| DrGonzalez | Shriner's Hospital | JoseGonz | Password890 | Video |
| AliceSmith | Shriner's Hospital | asmith39 | Password157 | Video, RDT, EMR |

| Entity | Software Program | Type | Version |
|--------|------------------|------|---------|
| Boston Medical Center | Zoom | Video | 5.5.1 |
| Boston Medical Center | Citrix Workspace | DV | 3.1.1 |
| Shriner's Hospital | Zoom | Video | 5.3.2 |
| Shriner's Hospital | ThriveUX | EMR | 1.4 |

| Key Site Information | _ | ▢ | X |

Boston Medical Center ← 752

Nursing Station: <u>Link</u>
Hospital Call Schedule: <u>Link</u>
Test or treatment Availability: <u>Link</u>     ← 754

Hospital IT Contact: 555-717-8765
Handoff Info: Signout will be done using the cart.

General Information:     ← 756

[ View ]    [ Send Feedback ]

Frequently Used Phone Numbers:     ← 756

[ View ]    [ Send Feedback ]

⋮

800

Platform Applications          _ □ X

802

808

Available Platform Applications:

810(1)          810(2)          810(3)

804          806

1000

1100

Figure 12:
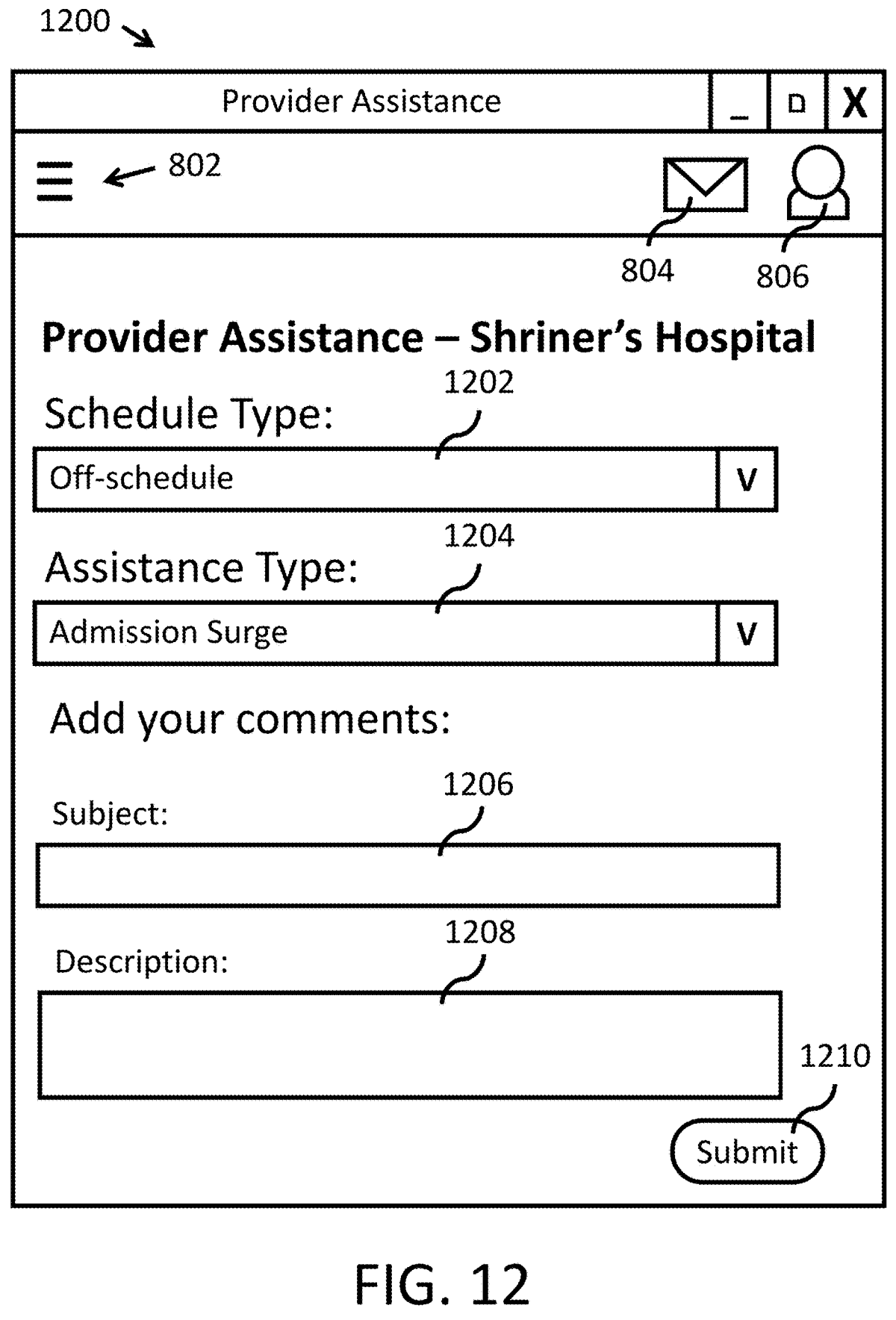

1200

Provider Assistance          _   □   X

☰ ← 802                                    ✉        👤

804        806

Provider Assistance – Shriner's Hospital

Schedule Type:          1202

Off-schedule                                    V

Assistance Type:          1204

Admission Surge                                V

Add your comments:

Subject:          1206

[                                              ]

Description:          1208

[                                              ]

1210

( Submit )

Receive, at a server, first login data from a client software application — 1302

Authenticate the remote worker user based on the login data — 1304

Receive command data from the client software application — 1306

Launch the selected software application — 1308

Input, using an RPA process, second login data of the remote worker user into the software application — 1310

1400

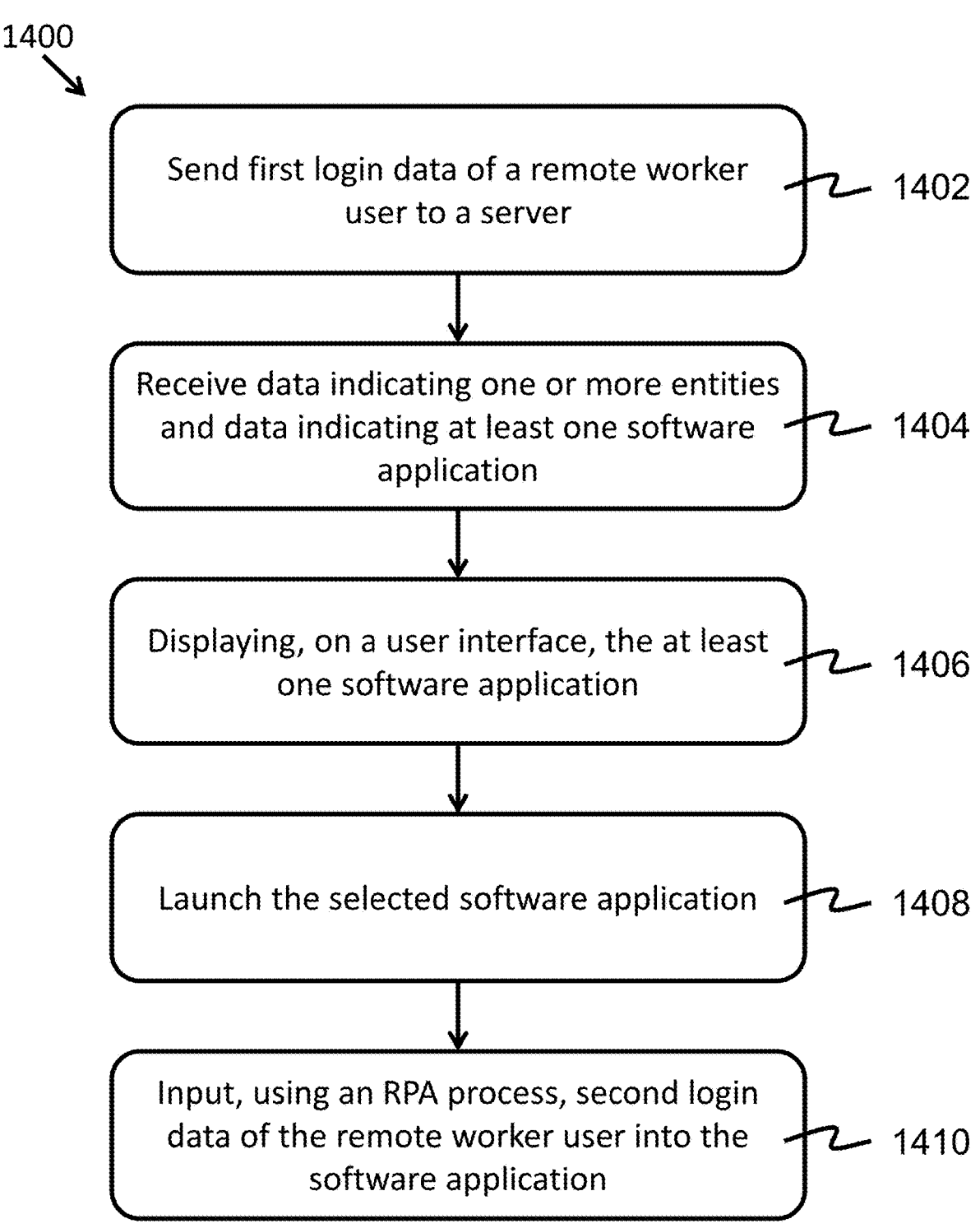

Send first login data of a remote worker user to a server — 1402

Receive data indicating one or more entities and data indicating at least one software application — 1404

Displaying, on a user interface, the at least one software application — 1406

Launch the selected software application — 1408

Input, using an RPA process, second login data of the remote worker user into the software application — 1410

Receive, at a server, first login data from a client software application — 1502

Authenticate the remote worker user based on the login data — 1504

Receive selection data, the selection data including an entity identifier — 1506

Retrieve entity data from a database based on the entity identifier — 1508

Send at least a portion of the entity data to a client software application — 1510

1600

Send first login data of a remote worker user to a server —— 1602

Receive data indicating one or more entities and data indicating at least one software application —— 1604

Detect a selection of a speech-to-text button on a user interface —— 1606

Open, on the user interface, a textbox configured to contain text data —— 1608

To FIG. 16B

1600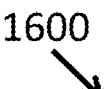
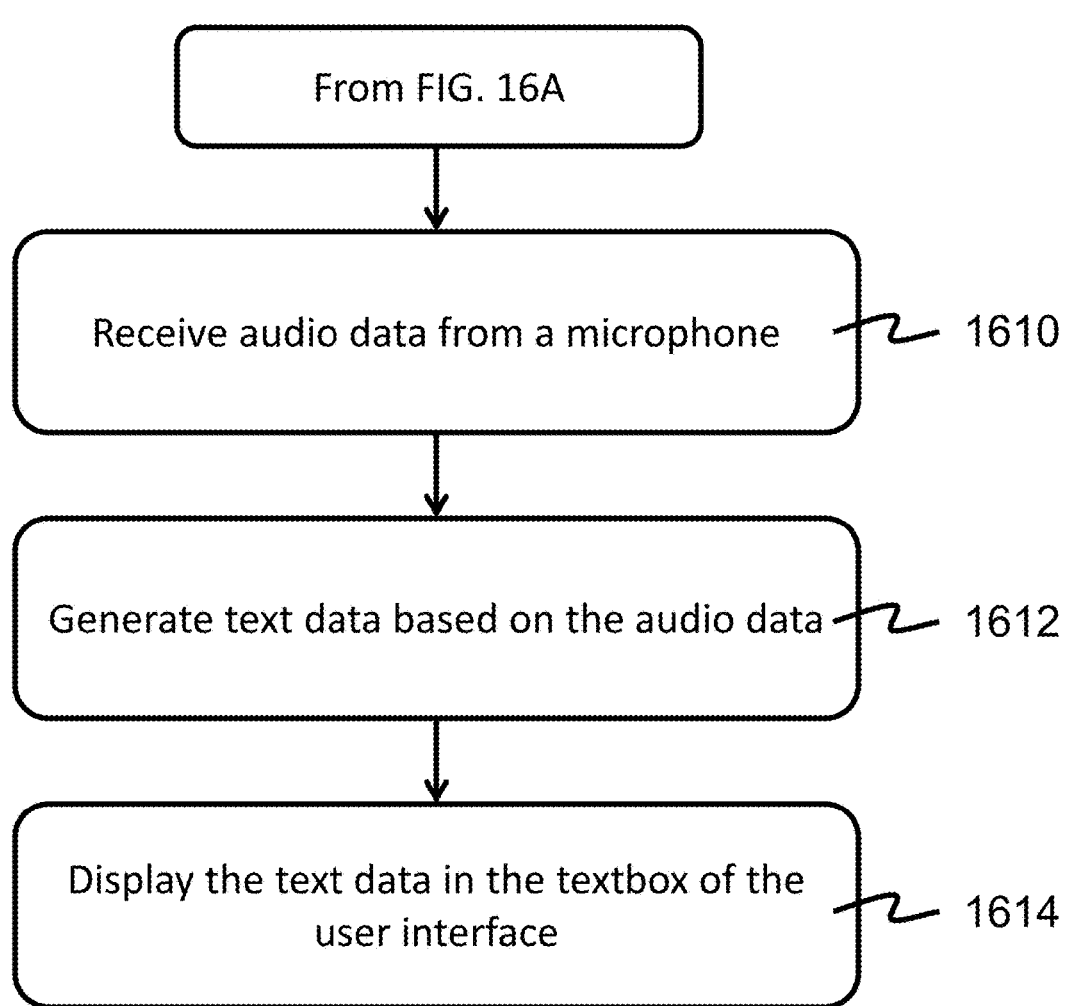
From FIG. 16A
Receive audio data from a microphone — 1610
Generate text data based on the audio data — 1612
Display the text data in the textbox of the user interface — 1614
FIG. 16B

1700

Send first login data of a remote worker user to a server — 1702

Authenticate the remote worker user based on the first login data — 1704

Receive a provider support data packet, including text data — 1706

Generate a second data packet that includes the text data — 1708

Send the second data packet to a second user device — 1710

SYSTEMS AND METHODS FOR AUTOMATING PROCESSES FOR REMOTE WORK

RELATED APPLICATIONS

This application is a continuation-in-part of U.S. patent application Ser. No. 17/454,464, entitled "Systems and Methods of Automating Processes for Remote Work," which was filed on Nov. 10, 2021, and which is pending; which is a continuation of U.S. patent application Ser. No. 17/444, 659, entitled "Systems and Methods of Automating Processes for Remote Work," which was filed on Aug. 6, 2021, and which is pending; which is a continuation of U.S. patent application Ser. No. 17/444,658 entitled "Systems and Methods of Automating Processes for Remote Work," which was filed on Aug. 6, 2021, and which is pending; which is a continuation of U.S. patent application Ser. No. 17/444, 657, entitled "Systems and Methods of Automating Processes for Remote Work," which was filed on Aug. 6, 2021, and which is pending. The entirety of these applications are incorporated by reference.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND OF THE DISCLOSURE

The present disclosure generally relates to remote computer systems, and more particularly to systems and methods of automating processes for remote work.

Working remotely has become more common than ever before. However, working remotely has its own technical challenges that can impede the remote work. One challenge is that a remote worker may need to interact with several different entities, and each entity may use a different proprietary software to provide access to that entity's systems. The different entities also require the user to maintain multiple login credentials needed to log into the different systems.

Additionally, each entity may use different software applications to perform functions on the system. These software applications may include video conferencing, remote desktop or other remote access software, database access, and other types of software applications. In order to work remotely, the remote worker needs to, among other things, (1) maintain login information for each of the different entity systems' software applications, (2) assure that each software application used to work remotely is up-to-date and compatible with the different entities' systems, and (3) must learn how to use each of the different entities' systems, which may vary greatly. All of these, and more, present technical challenges to the remote worker.

What is needed are technical solutions to the technical problems stated above, as provided by systems and methods of automating processes for remote work.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the disclosure is a non-transitory computer-readable storage medium having executable instructions stored thereon. The executable instructions, when executed by a processor, may be configured to perform one or more steps. The one or more steps may include receiving, at a server, first login data from a client software application executing on a user device of a remote worker user. The steps may include authenticating the remote worker user based on the first login data. The steps may include receiving, at the server, command data from the client software application. The command data may include data indicating to the server to launch a software application. the steps may include launching, on the server, the software application. The steps may include inputting, using a robotic process automation (RPA) process, second login data of the remote worker user into the software application.

One aspect of the disclosure is a method. The method may include a method of automating processes for remote work. The method may include receiving, at a server, first login data from a client software application. The client software application may be executing on a user device of a remote worker user. The method may include authenticating the remote worker user based on the first login data. The method may include receiving, at the server, command data from the client software application. The command data may include data indicating to the server to launch a software application. The method may include launching, on the server, the software application. The method may include inputting, using an RPA process, second login data of the remote worker user into the software application.

Another aspect of the disclosure is another method of automating processes for remote work. The method may include sending, to a server, first login data of a remote worker user. The first login data may include a username and a password hash. The method may include receiving, from the server, data indicating one or more entities and data indicating at least one software application associated with at least one entity of the one or more entities. The method may include displaying, on a user interface, the at least one software application. The user interface may include a user interface of a software application of a user device. The method may include launching the selected software application. The method may include inputting, using a RPA process, second login data of the remote worker user into the selected software application.

Another aspect of the disclosure includes another non-transitory computer-readable storage medium having executable instructions stored thereon. The executable instructions, when executed by a processor, are configured to perform one or more steps. The one or more steps may include receiving, at a server, first login data from a client software application executing on a user device of a remote worker user. The one or more steps may include authenticating the remote worker user based on the first login data. The one or more steps may include receiving, at the server, selection data from the client software application. The selection data may include an entity identifier. The one or more steps may include retrieving entity data from a database in data communication with the server. The retrieval of the entity data may be based on the entity identifier. The one or more steps may include sending at least a portion of the entity data to the client software application.

Another aspect of the disclosure includes another non-transitory computer-readable storage medium having executable instructions stored thereon. The executable instructions, when executed by a processor, are configured to perform one or more steps. The one or more steps may include receiving, at a server, first login data from a client software application executing on a user device of an administrative user. The one or more steps may include authenticating the administrative user based on the first login data. The one or more steps may include receiving, at the server, selection data from the client software application. The selection data may include an entity identifier. The one or more steps may include receiving, at the server, first entity data from the client software application. The one or more steps may include updating, based on the first entity data and the entity identifier, a database in data communication with the server.

One aspect of the disclosure is a non-transitory computer-readable storage medium having executable instructions stored thereon. The executable instructions, when executed by a processor, may be configured to perform one or more steps. The one or more steps may include sending, to a server, first login data of a remote worker user. The first login data may include a username and a password hash. The one or more steps may include receiving, from the server, data indicating a plurality of entities and data indicating at least one software application associated with at least one entity of the plurality of entities. The one or more steps may include detecting a selection, from the remote worker user, of a speech-to-text button on a user interface. The one or more steps may include opening, on the user interface, a textbox configured to contain text data. The one or more steps may include receiving audio data from a microphone in data communication with the processor. The one or more steps may include generating text data based on the audio data. The text data may correspond to content of the audio data. The one or more steps may include displaying the text data in the textbox of the user interface. The one or more steps may include allowing the remote worker user to make edits to the text data or copy and paste portions of the text data to a software application, such as an electronic medical records database entry.

Another aspect of the disclosure may include licensing and credentialing onboarding of a remote worker user. This may include configuring one or more accounts for the remote worker user regarding one or more entities or one or more entity systems. Configuring the one or more accounts may include the remote worker user sending data to a server. The data may include a desired username, password, or other account data. Configuring the one or more accounts may include the remote worker user uploading files to the server, the remote worker user sending the files via email, or the remote worker user filling out a form in a file and uploading the file to the server.

Another aspect of the disclosure may include a non-transitory computer-readable storage medium having executable instructions stored thereon. The executable instructions, when executed by a processor, may be configured to perform one or more steps. The one or more steps may include receiving, at a server, first login data from a client software application executing on a first user device of a first remote worker user. The first remote worker user may include a medical provider user. The one or more steps may include authenticating the first remote worker user based on the first login data. The one or more steps may include receiving, from the client software application, a provider support data packet. The provider support data packet may include text data. The one or more steps may include generating a second data packet. The second data packet may include the text data. The one or more steps may include sending the second data packet to a second user device of a second remote worker user. The second remote worker user may include a medical provider user.

One aspect of the disclosure may include another non-transitory computer-readable storage medium having executable instructions stored thereon. The executable instructions, when executed by a processor, may be configured to perform one or more steps. The one or more steps may include receiving, at a server, first login data from a client software application executing on a first user device of a first remote worker user. The one or more steps may include authenticating the first remote worker user based on the first login data. The one or more steps may include receiving, from the client software application, an information technology support data packet. The information technology support data packet may include a help ticket. The help ticket may include first text data indicating a subject of the help ticket, and second text data indicating a description of the help ticket. The one or more steps may include generating a second data packet. The second data packet may include the first text data and the second text data. The one or more steps may include sending the second data packet to an administrative user.

Another aspect of the disclosure includes activity logging. Activity logging may aid in data privacy compliance regarding storing and transmitting data. Activity logging may also aid a remote worker user's workflow when performing tasks for certain entities. Activity logging may include a remote worker user creating a log entry on the remote worker user's computing device. The computing device may be in data communication with a server. The computing device may send the log entry to the server and may encrypt the log entry to prevent unauthorized viewing of the activity log. The computing device and server may also allow the remote worker user to view past log entries, edit past log entries, filter a list of log entries by certain criteria, generate and export a report of log entries, or use log entries for payroll or reimbursement purposes.

Numerous other objects, advantages and features of the present disclosure will be readily apparent to those of skill in the art upon a review of the following drawings and description of various embodiments.

BRIEF DESCRIPTION OF THE DRAWINGS

FIG. 5 is a schematic view illustrating one embodiment of a database table for a system of automating processes for remote work.

FIG. 6 is a schematic view illustrating another embodiment of a database table for a system of automating processes for remote work.

FIG. 7A is a schematic view illustrating another embodiment of a database table for a system of automating processes for remote work.

FIG. 12 is a front view illustrating one embodiment of a user interface of a software application of a user device for a system of automating processes for remote work.

FIG. 14 is a flowchart illustrating one embodiment of a method of automating processes for remote work.

FIG. 16B is a continuation of the flowchart of FIG. 16A illustrating one embodiment of a method of automating processes for remote work.

DETAILED DESCRIPTION

The present disclosure is directed to systems and methods of automating processes for remote work. The platform provides a uniform interface for a remote worker to interact with the different systems of multiple entities, even where such systems vary greatly from entity to entity. The platform leverages the entities' existing technology infrastructures and eliminates the costly and complex process of integrating each new remote user to each entity's system. The platform eliminates the burden of the remote worker of managing processes and systems at the multiple entities.

Figure 1:
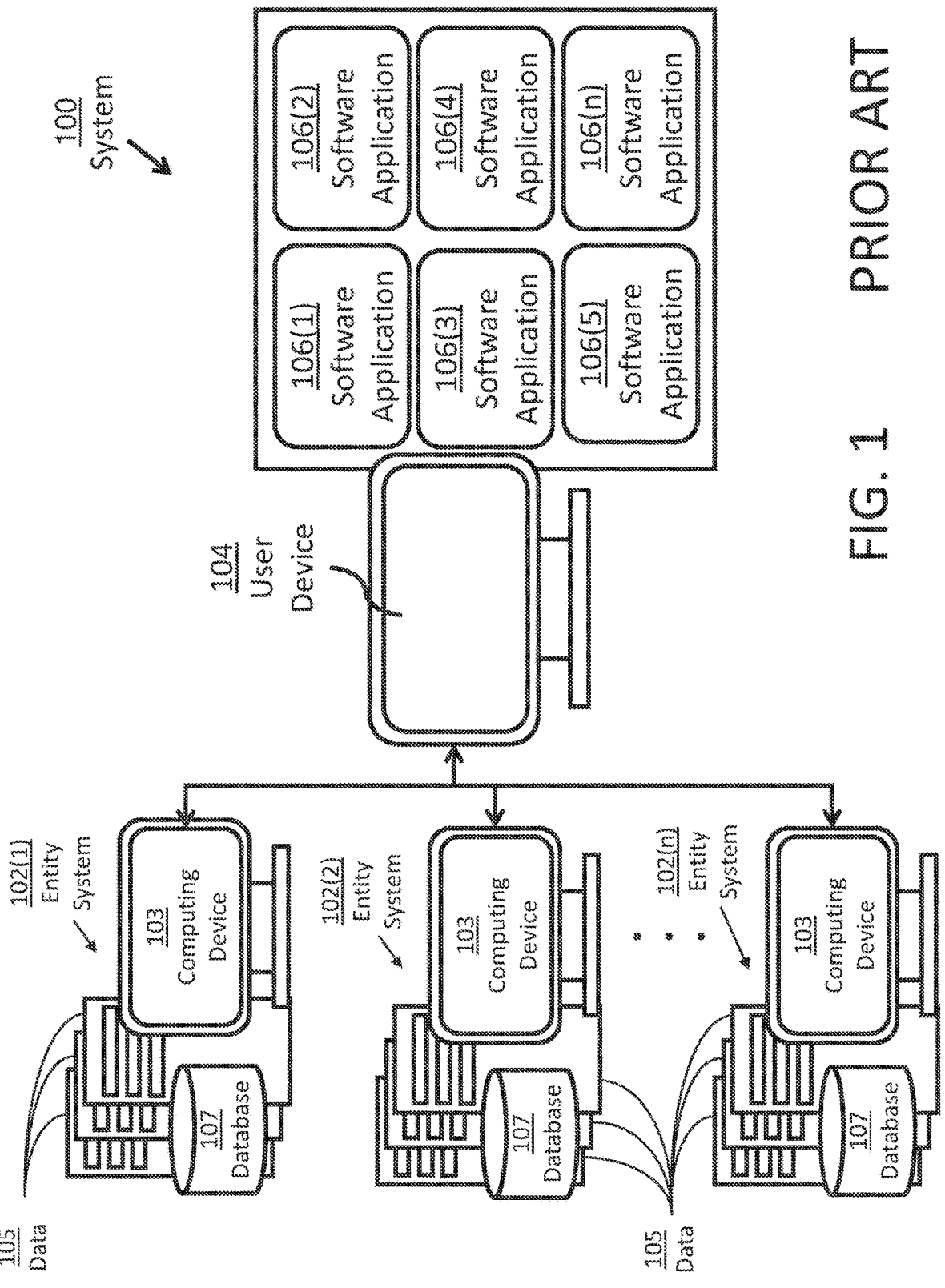
FIG. 1 is a schematic view illustrating one embodiment of a prior art system.

FIG. 1 depicts a prior art system 100. The system 100 may include one or more entity systems 102(1)-(n) and a user device 104. The user device 104 may include one or more software applications 106(1)-(n). The one or more entity systems 102(1)-(n) and the user device 104 may be in data communication with each other over one or more data networks, e.g., the Internet.

Each entity system 102 of the one or more entity systems 102(1)-(n) may include a computing system with various computing devices networked together. The entity system 102 may allow an external computing device (e.g., the user device 104) to communicate with a portion of the entity system 102 to perform some functionality within the entity system 102. Such functionality may include remote desktop functionality, accessing data stored in a database of the entity system 102, or video conferencing functionality.

In order to access such functionality in the entity system 102, a user of the user device 104 must have the proper software application 106 installed on the user device 104. As the different entity systems 102(1)-(n) may use different software to carry out the functionality previously mentioned, the user device 104 must have all of the different software applications 106(1)-(n) to access the functionality.

There are many disadvantages to the prior art system 100. The user of the user device 104 must keep track of the login information (e.g., username and password) for each of the software applications 106(1)-(n). The user of the user device 104 must also make sure that each of the software applications 106(1)-(n) is the correct version such that it is compatible with the entity systems 102(1)-(2). This can be impossible if two different entity systems 102 use two incompatible versions of the same software application. Furthermore, each software application 106 has its own user interface, user experience, and nuances that the user of the user device 104 must learn, which takes away from the user's time that could be spent performing substantive work.

As an example, the one or more entity systems 102(1)-(n) may include hospital computer systems. Each hospital computer system may have its own computing devices, electronic medical records (EMR) database, and software used to interact with the hospital computer system. The user device 104 may include a physician's computer. The physician may care for patients at multiple different hospitals. The physician may use his or her user device 104 to connect to a hospital computer system 102 and perform various functionality. For example, the physician may use a remote desktop application installed on the user device 104 to remote into the computer hospital system 102. The physician may use a video conferencing application to virtually visit with patients in the hospital. The patients may use a mobile device to video chat with the physician or may use a mobile medical cart with a computer to virtually visit with the physician. The physician may use a database application installed on the user device 104 to access EMRs stored in the hospital computer system 102. Performing all of this functionality with the software applications 106(1)-(n) includes the same disadvantages as previously discussed.

Figure 2:
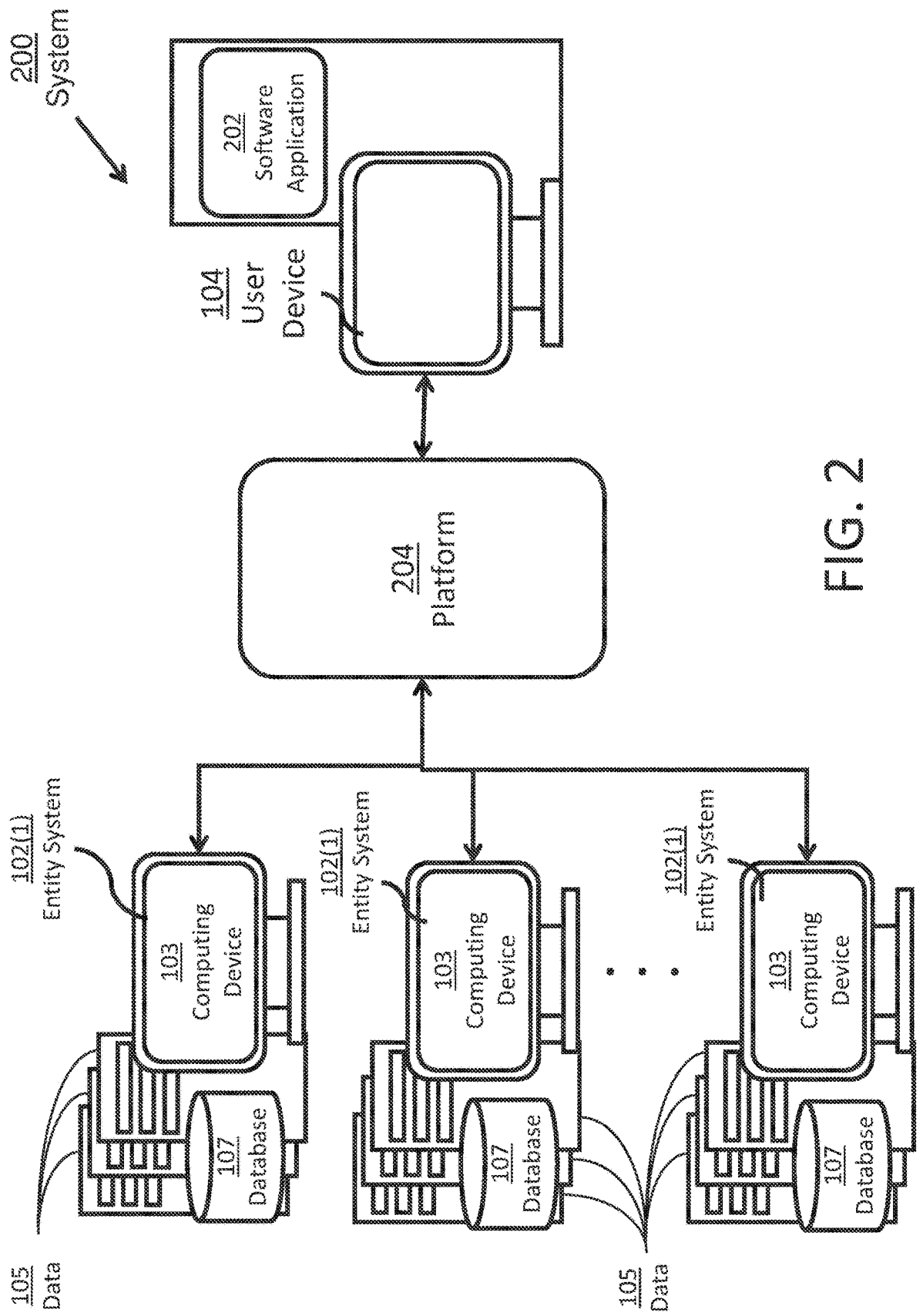
FIG. 2 is a schematic view illustrating one embodiment of a system of automating processes for remote work.

FIG. 2 depicts one embodiment of a system 200. The system 200 may include a system of automating processes for remote work. The system 200 may include the entity systems 102(1)-(n), which may be similar to the entity systems 102(1)-(n) of the prior art system 100. The system 200 may include the user device 104. The user device 104 may be similar to the user device 104 of the prior art system 100. However, instead of having the multiple, different software applications 106(1)-(n) installed on the user device 104, the user device may only include a single software application 202.

The system 200 may include a platform 204. The platform 200 may be in data communication with the user device 104 and the one or more entity systems 102(1)-(n) over a data network. The platform 204 may include software that may facilitate interaction between the entity systems 102(1)-(n) and the user device 104. This may include providing a single sign-on (SSO) login between the user device 104 and the entity systems 102(1)-(n). This may include managing versions of the software applications used for interacting with the entity systems 102, including maintaining different versions of the same software application. This may include providing a single user interface for the same functionality, even if different entity systems 102(1)-(n) use different software applications to provide that functionality.

As an example, again, the one or more entity systems 102(1)-(n) may include hospital computer systems, and the user device 104 may include a physician's computer. However, the user device 104, instead of including software applications 106(1)-(n), may include a single software application 202, which may include a software application used to interact with the platform 204. The physician may enter his or her login information into the software application 202 to log into the platform 204. The platform 204 may include multiple software applications that may allow the physician to interact with the hospital computer systems 102(1)-(n), for example, via desktop virtualization, video conferencing, or EMR access.

In this example, the physician using the software application 202 and the platform 204 may not experience the disadvantages of the prior art system 100. The physician may only need to maintain one set of login credentials, i.e., the login credentials for the platform 204. The platform 204 may maintain the login credentials between the physician and the different hospital entity systems 102(1)-(n). The platform 204 may maintain all the software applications for interacting with the hospital computer systems 102(1)-(n), including remote desktop applications, video conferencing applications, EMR database access applications, and other software applications. The platform 204 may provide a uniform user interface for the physician such that two different hospital computer systems 102(1)-(n) may use two different video conferencing applications with two different user interfaces, but the platform 204 may present the video conferencing functionality uniformly to the physician.

Further details about the systems and methods of automating processes for remote work will now be provided. In one embodiment, each entity system 102 of the one or more entity systems 102(1)-(n) may include a computer system. The computer system may include one or more computing devices, such as desktop computers, laptop computers, mobile computing devices (e.g., a mobile phone or tablet computer), mobile medical carts with a computer installed on the cart, application servers, database servers, and other computing devices. The computing devices may be in data communication with each other over a data network, such as a local area network (LAN) or a wide area network (WAN).

In one embodiment, an entity system 102 may include one or more software applications. A software application may be installed on a computing device of the entity system 102. The software application may include a client application that may interact with a server to perform at least a portion of the software application's functionality. The entity system 102 may include the server, or the server may be external from the entity system 102.

One type of software application of the entity system 102 may include remote desktop application. A remote desktop application may include a software application configured to allow a computer desktop environment to execute remotely while being displayed on a separate computing device. The remote desktop application may accept input from the computing device displaying the desktop environment, send that input data to the remote computing device where the desktop environment is executing, and may update the displayed desktop based on the remote computing device's execution.

Another type of software application of the entity system 102 may include a video conferencing application. A video conferencing application may include a software application that transmits audio and video data between computing devices in real time and reproduces the received audio and video data such that users in different locations can communication and view each other in real time.

In some embodiments, the entity system 102 may include an EMR database application. An EMR database application may include a software application that can create, access, or modify EMRs that are stored in an EMR database. The software application may display an EMR for viewing on the user device 104. The software application may accept input form the user device 104, and the software application may transmit that input to the EMR database to modify the EMR stored therein.

In one embodiment, the entity system 102 may include a remote vital signs measurement application. A remote vital signs measurement application may receive data from a vital signs measurement device, process the received data, and transmit the processed data to another software application or another device. For example, an entity system 102 may include a digital stethoscope. The digital stethoscope may auscultate a patient and send the auscultation data to the remote vital signs measurement application via the entity system's 102 data network. The remote vital signs measurement application may process the received auscultation data, and send it to the user device 104 of the physician so that the remote physician may hear the patient's heartbeat remotely. A vital signs measurement device may include a networked electrocardiograph (ECG) machine, a digital stethoscope, or other device capable of measuring or receiving patient vital signs. In one or more embodiments, the entity system 102 may include other types of software applications.

In one embodiment, the user device 104 may include a computing device. The computing device may include a desktop computer, laptop computer, tablet computer, mobile phone, or other computing device. The user device 104 may include a video camera. The video camera may record or stream video data. The user device 104 may include a microphone. The microphone may record or stream audio data. The user device 104 may include an audio output device. The audio output device may include speakers, headphones, or other audio output devices that may reproduce audio data.

In some embodiments, the user device 104 may include the software application 202. The software application 202 may include a remote access application. The remote access application may be in data communication over a data network with the platform 204. The remote access application may be configured to allow the user of the user device 104 to control at least a portion of the execution of a computing environment of the platform 204 remotely. The remote access application may be further configured to display, on the user device 104, a user interface to assist the user in remotely controlling that computing environment of the platform 204.

In some embodiments, the user device 104 may remotely control the execution of the computing environment of the platform 204 using desktop virtualization. Desktop virtualization may separate the desktop environment of a computing device and its associated software applications from the physical computing device used to access those environment and applications. The desktop virtualization may include a client-server architecture. As such, application execution may occur on the platform 204 (the "server") and may communicate with the remote access application (the "client") of the user device 104 using a remote display protocol through which the user of the user device 104 may interact with the application executing on the platform 204. Input/output information (e.g., display information, mouse clicks, keyboard strokes, touchscreen interactions, etc.) may be communicated between the platform 204 and the remote access application to control the application executing on the platform 204 and display information regarding the application on the user device 104. In some embodiments, the remote access application may include a remote desktop application.

In some embodiments, the remote access application may include a web browser. The web browser may accept input from the user and send that input to the platform 204, and the platform 204 may receive the input and execute functionality on the platform 204 based on that input. The platform 204 may send display information to the web browser to display information to the user. In one or more embodiments, the remote access application may include another type of software application other than desktop virtualization, remote desktop, or a web browser that may allow a user of the user device 104 to control at least a portion of a computer environment of the platform 204 and display information about that environment on the user device 104.

In one embodiment, the software application 202 may include login functionality. The login functionality may allow the user of the user device 104 to enter login data. The login data may include a username, password, or other login data. The software application 202 may process the login data (e.g., hashing the password) and send the processed login data to the platform 204 for authentication. In response to the user entering the correct login data, the platform 204 may authenticate the user device 104 and log the user device 104 into the platform 204.

Figure 3A:
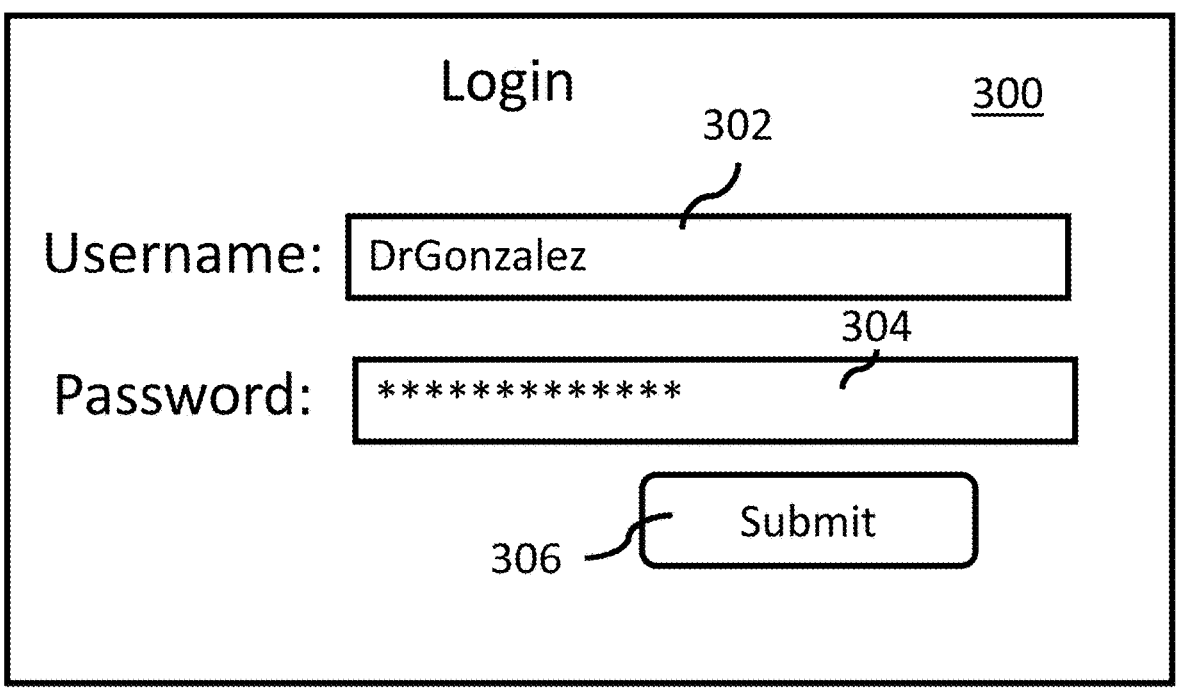
FIG. 3A is a front view illustrating one embodiment of a user interface appearing on a software application of a user device of a system of automating processes for remote work.

FIG. 3A depicts one embodiment of a login screen 300 that may appear on the user device 104 based on the login functionality of the software application 202. The login screen 300 may include a first textbox 302 where the user may enter his or her username for using the platform 204. The login screen 300 may include a second textbox 304 where the user may enter his or her password associated with the username for using platform 204. The login screen 300 may include a submit button 306. In response to the user interacting with the submit button 306, the software application 202 may process the entered login data and submit it to the platform 204 to authenticate the user.

In one embodiment, logging into the platform 204 may include using multi-factor authentication ("MFA"). MFA may include two-factor authentication. MFA may include granting access to the platform 204 only after successfully presenting multiple pieces of evidence ("authentication factors") to authenticate the user. In one embodiment, one authentication factor may include a username and password. An authentication factor may include sending a personal identification number (PIN) to an email address controlled by the user. An authentication factor may include sending a PIN to a mobile phone of the user (which may include the user device 104) via short message service (SMS) or some other messaging service. An authentication factor may include a one-time password (OTP) that may be time-synchronized with the platform 204, and the user may obtain the OTP from a security token device or a software application. An authentication factor may include a biometric factor such as a fingerprint, a face scan, an eye scan, or some other biological trait unique to the user. Other types of authentication factors are contemplated by the disclosure.

Figure 3B:
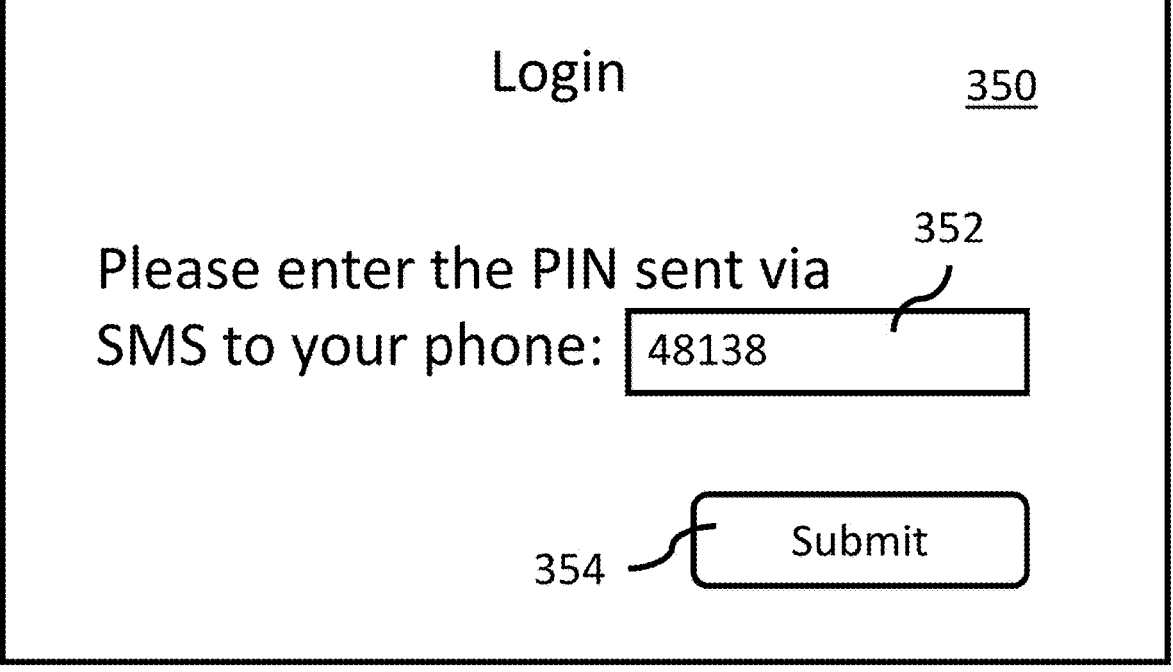
FIG. 3B is a front view illustrating another embodiment of a user interface appearing on a software application of a user device of a system of automating processes for remote work.

FIG. 3B depicts one embodiment of a login screen 350. The login screen 350 may appear on the user device 104 after the user successfully authenticates with a username and password on the login screen 300. The login screen 350 may include a textbox 352 for entering a PIN. The user may obtain the PIN, as suggested by the login screen 350, from a SMS message sent to the user. The platform 204 may cause the SMS message with the PIN to the be sent to the user in response to the user successfully authenticating with the username and password using the login screen 300. In response to the user successfully entering the PIN, the platform 204 may log the user into the platform 204.

In one embodiment, the login functionality of the software application 202 may include detecting if the user is already logged in. Detecting whether the user is already logged in may include detecting a Secure Assertion Markup Language (SAML) session in the software application 202. The SAML session may include authentication or authorization, which may include login data or data based on login data. The software application 202 may send SAML session data to the platform 204, and the platform 204 may log in the user into the platform 204. In some embodiments, the software application 202 using the SAML session data to log in may allow the user to log in without having to enter login information as described above in relation to FIG. 3A and FIG. 3B.

In some embodiments, the login functionality of the software application 202 may be applicable to multiple types of users. In some embodiments, the types of users of the platform 204 may include a remote worker user. A remote worker user may include a user who uses the platform 204 to interact with the one or more entity systems 102(1)-(n). The types of users of the platform 204 may include an administrative user (sometimes referred to as an "admin user"). An administrative user may include a user who interacts with the platform 204 to effect changes on the platform 204, assist remote worker users, or other functionality. Further details and examples of the different operations that remote worker users, admin users, and other types of users can perform on the platform 204 will be discussed below.

Figure 4:
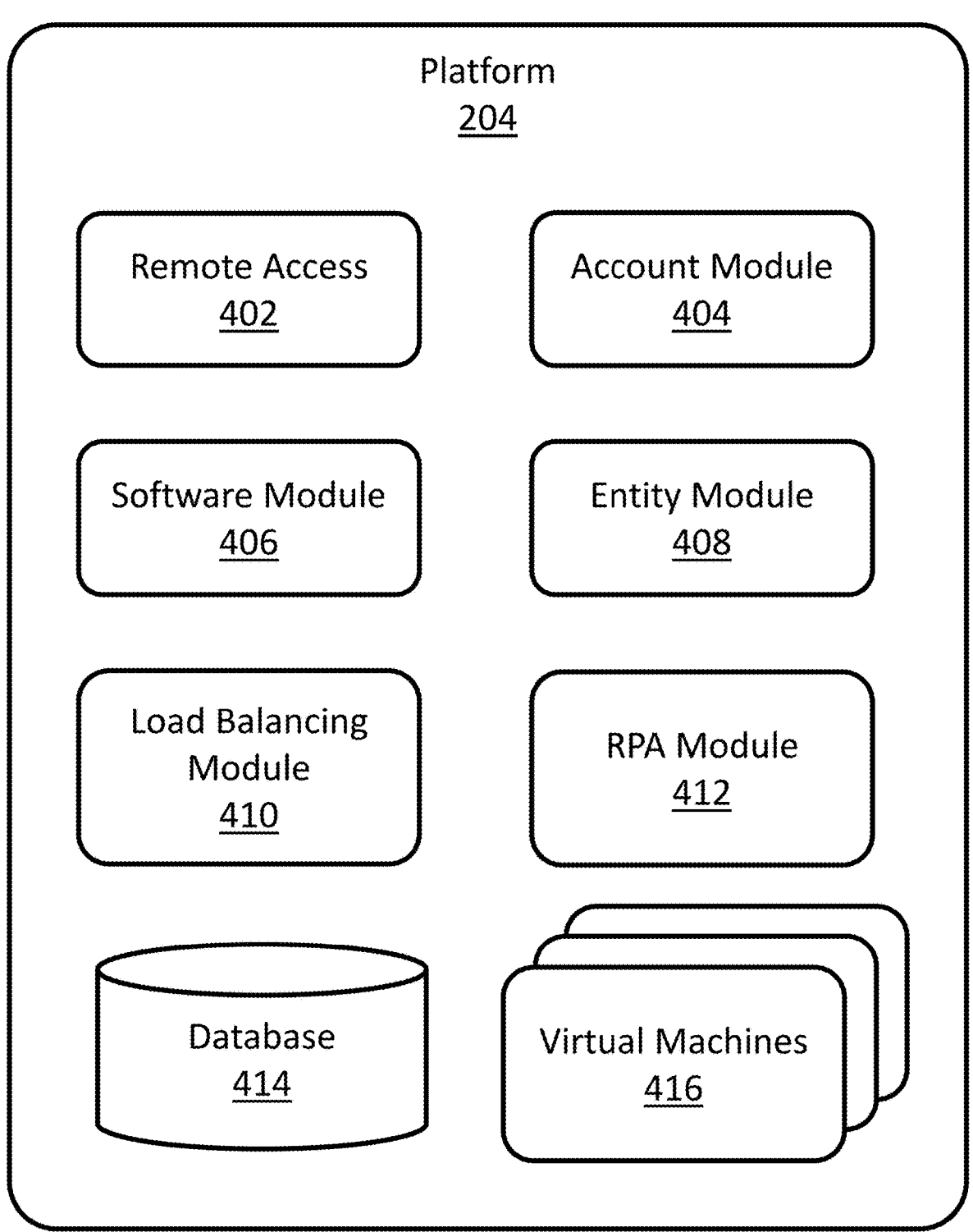
FIG. 4 is a schematic view illustrating one embodiment of a platform for a system of automating processes for remote work.

FIG. 4 depicts one embodiment of the platform 204. The platform 204 may include a combination of software and hardware. The platform 204 may include one or more computing devices. A computing device may include a desktop computer, a laptop computer, a mobile computing device, an application servers, a database server, or other computing devices. The computing devices may be networked together into a computer system. The platform 204 may include one or more software modules 402-412 that may be stored on or execute on the computing devices of the platform 204. The platform 204 may include a database 414. The platform 204 may include one or more virtual machines 416. In some embodiments, all or part of the modules 402-412, the database 414, or the virtual machines may be stored or executed on a computing device external from the platform 204, such as an external server or a cloud computing server.

In one embodiment, the platform 204 may include a remote access module 402. The remote access module 402 may control the platform's 204 side of the remote access functionality of the system 200. The remote access module 402 may include the "server" side of the desktop virtualization or remote desktop client-server architecture. The remote access module 402 may receive input data from the software program 202 (e.g., mouse click data, keyboard stoke data, touchscreen interaction data, data from a browser, etc.), process the received data, and send the processed data to a software application executing on the platform 204. The remote access module 402 may receive data from the software application executing on the platform

204, process the received data, and send display data to the software program 202 to be displayed on the user device 104.

In one embodiment, the platform 204 may include an account module 404. The account module 404 may perform functionality related to maintaining one or more accounts for one or more users of the platform 204. One type of account the account module 404 may maintain is referred to as a "platform user account." A platform user account may include the overarching account that a remote worker user of the platform 204 may use to interact with the platform 204 and perform functionality on the platform 204. A remote worker user may log into his or her platform user account using the login functionality described above in relation to FIGS. 3A-B.

In some embodiments, another type of account the account module 404 may maintain is referred to as an "entity user account." An entity user account may include an account that a remote worker user may maintain or user in order to interact with an entity system 102. In some embodiments, an entity system 102 may include a single entity user account that a remote worker user may use to interact with the entity system 102. For example, a remote worker user may use that single entity user account in order to use the entity system's 102 video conferencing functionality, remote desktop functionality, and EMR access functionality. In some embodiments, an entity system 102 may include multiple entity user accounts for different entity system 102 functionality. For example, a remote worker user may user a first entity user account to use the first entity system's 102(1) video conferencing functionality and may use a second user entity account to use the first entity system's 102(1) EMR access functionality.

In one or more embodiments, a remote worker user's platform user account may include or be associated with one or more entity user accounts. The account module 404 may maintain the one or more entity user accounts associated with the platform user account such that the remote worker user may only need to maintain the information of the remote worker user's platform user account. This may include the account module 404 maintaining the login information for the remote worker user's entity user accounts so that the remote worker user does not need to remember his or her login information for all of his or her entity user accounts, only his or her platform user account. In some embodiments, the accounts module 204 may use information stored in relation to the remote worker user's platform user account to generate or maintain information associated with the remote worker user's one or more entity user accounts.

Another type of account the account module 404 may maintain is referred to as a "administrator user account" or an "admin account." An admin account may include an account on the platform 204 that a admin user of the platform 204 may use to interact with the platform 204 and perform functionality on the platform 204. An admin user may log into his or her admin account using the login functionality described above in relation to FIGS. 3A-B.

In some embodiments, the account module 404 may use the database 414 to store and retrieve information associated with the platform user accounts, the entity user accounts, the admin accounts, or other types of user accounts. The database 414 may include one or more database management systems (DBMS). A DBMS may include a relational database, object-oriented database, NoSQL database, or some other type of DBMS. Each DBMS may include associated data structures such as tables, rows, columns, indices, etc.

In some embodiments, the account module 404 may interact with the remote access module 402 to authenticate the user device 104. For example, in response to receiving a username and password hash from a user device 104 (whether from a remote worker user, an admin user, or another type of user), the remote access module 402 may send the received username and password hash to the account module 404. The account module 404 may check the username and password hash against the database 414 to determine if the username and password hash match the data of a platform user account in the database 414. If so, the account module 404 may notify the remote access module 402 whether the received data matched.

FIG. 5 depicts one embodiment of a database table 500. The table 500 may be stored in the database 414. The table 500 may include a table of platform user accounts. The table 500 may store information associated with a user's platform user account. In some embodiments, the table 500 may include a user's username 502. The username 502 may include the username of the user on the platform 204. The username 502 may uniquely identify the user among the other users of the platform 204. The table 500 may include the user's password hash 504. The username 502 and password hash 504 may be used to authenticate the user as described in relation to FIGS. 3A-B. The table 500 may include demographic information about the user. For example, the table 500 may include the user's first name 506, the user's last name 508, the user's birthday 510, other demographic information, contact information (e.g., a physical address, an email address, a phone number) (not shown). The table 500 may include information about the user that may be pertinent to the one or more entity systems 102(1)-(n). For example, as shown in FIG. 5, where the entity systems 102(1)-(n) may include hospital computer systems, the table 500 may include information where the user is licensed to practice medicine 512. Such information may include one or more jurisdictions (e.g., countries, national subdivisions, etc.). Other information may be stored in the table 500 or may linked to the data in the table 500. For example, in some embodiments, instead of the licensing data 512 being stored in the table 500, the licensing data 512 may be stored in a separate table and linked to the table 500 using the username 502 as a foreign key.

Although not depicted in the Figures, the database 414 may store a database table that may include a table of admin accounts. The admin accounts table may include data similar to the table 500, such as a username 502 of the admin user account, a password hash 504, a first name 506, a last name 508, demographic information (such as a birthdate 510), or other information. The admin account table may not include licensing data 512, but may include other data useful for admin users, such as permissions regarding functionality that the admin user can perform on the platform 204. In some embodiments, the database 414 may store the platform user accounts, the admin accounts, or other types of accounts in a single table. The single table may include data that may distinguish the different types of accounts.

FIG. 6 depicts one embodiment of a database table 600. The table 600 may be stored in the database 414. The table 600 may include a table of entity user accounts. The table 600 may store information associated with a remote worker user's one or more entity user accounts. In one embodiment, the table 600 may include a remote worker user's username 602 associated with that remote worker user's platform user account. For example, as depicted in FIG. 6, the first three rows of the table 600 each include the username 602 "DrGonzalez." The first three rows of the table 600 may include entity user account information associated with the platform user account described in the first row of the table 500 of FIG. 5 since the username 602 of the table 600 matches the username 502 of the table 500. The username 602 may include a foreign key of the table 500.

The table 600 may include an entity 604. The entity 604 may include information that identifies an entity associated with the user identified by the username 602. For example, as shown in FIG. 6, an entity 604 may include a hospital that operates one of the entity systems 102(1)-(n). The table 600 may include an entity username 606. An entity username 606 may include a username for the user on the entity's 604 entity system 102. In some embodiments, the username 602 and the entity username 606 may match. For example, as shown by the first row of the table 600 in FIG. 6, the user's username is "DrGonzalez" for both the platform 204 and the entity system 102 associated with "Boston Medical Center." In some embodiments, the username 602 and the entity username 606 may not match. For example, as shown by the second row of the table 600, the user's username 602 is "DrGonzalez" but the user's entity username 606 (i.e., the user's username in the "Massachusetts General Hospital" entity system 102) is "JoseGonz."

The table 600 may include an entity password 608. The entity password 608 may include the user's password on that entity's 604 entity system 102 and that is associated with the user's username 606 on the entity's 604 entity system 102. The password 608 may include the actual password and not a hash (as was the case in the table 500) so that the platform 204 can log the user into the associated entity system 102 (discussed further below).

The table 600 may include one or more functions 610 that the user's entity user account is capable of on the associated entity system 102. For example, as shown in the first row of the table 600 of FIG. 6, the user associated with the platform user account identified by the username "DrGonzalez," when using the entity system 102 associated with the entity 604 "Boston Medical Center" is able to use video conferencing functionality ("Video"), remote desktop functionality ("RDT"), and EMR access functionality ("EMR"). Different entity user accounts may include different functionality, even for the same user. For example, as shown in the third row of the table 600, the user "DrGonzalez" only has video conferencing functionality when using the entity system 102 of the entity 604 "Shriner's Hospital." It should be noted that in some embodiments, instead of the functionality data 610 being stored in the table 600, the functionality data 610 may be stored in a separate table and linked to the table 600 using some of the data (e.g., the username 602, the entity 604, or the entity username 606) as a foreign key.

In some embodiments, a module of the platform 204 (such as the account module 404 or the entity module 408) may be configured to onboard a remote worker user of the platform 204 for an entity system 102. Onboarding a remote worker user may include configuring a platform user account or one or more entity user accounts for use by the remote worker user. In one embodiment, configuring the platform user account for the remote worker user may include the remote worker user sending information about the remote worker user to the platform 204. The information may include a desired username or password, the remote worker user's name or demographic information, licensing information, the remote worker user's contact information (e.g., email address, phone number, physical address, etc.), or other information. The remote worker user may send this information to the platform 204 using the software application 202 (e.g., via an account creation webpage using a browser or an account creation screen using a mobile application). The remote worker may send this information to the platform 204 by uploading files to the platform 204 (e.g., a transcript, a certification, a photo identification document, etc.). The remote worker user may email the information to an email address associated with the platform 204. In some embodiments, the platform 204 may send documents to the remote worker user (e.g., via an email to the remote worker user, via a download accessible via a webpage, or via an internal messaging service of the platform 204), and the remote worker may fill out the documents and return them to the platform 204. The platform 204 may store the returned document, e.g., in the database 414 or in some other data storage. In some embodiments, a module of the platform may automatically generate a platform user account or one or more entity user accounts using the data received from the remote worker user. In other embodiments, an admin user may use the received data to generate a platform user account or one or more entity user accounts for the remote worker user (e.g., via an account creation webpage or screen accessible to the admin user).

In some embodiments, an admin user may use the account module 404 or the entity module 408 to customize the onboarding process for a specific user or a type of user. A type of user may include a user at a specific location, a user with a specific role, or a user that belongs to some other type. The onboarding process, including the onboarding information requested from or received from a remote user, may be different for different remote users or for different types of remote users. In one embodiment, the account module 404 or the entity module 408 may interact with an application programming interface (API) to receive information about the remote working that is being onboarded. The API may include an API for a system that stores information about the remote worker. For example, the API may include an API for a system that stores medical credential information for physicians. The account module 404 or the entity module 408 may request information from an API automatically or at a certain time interval. The automated requesting of information from the API may allow the account module 404 or the entity module 408 to keep the remote worker's information up-to-date.

The platform 204 may include a software module 406. The software module 406 may perform functionality related to maintaining one or more software applications used by the platform 204. The software applications may include software applications that may allow a user to interact with an entity system 102. The software applications may include a video conferencing application, a remote desktop application, a EMR access application, or other types of software applications. The software module 406 may include functionality such as configuring a virtual machine 416 to execute a software application, maintaining different versions of the same software application, and associating an entity system 102 with one or more of the software applications. In some embodiments, an admin user may use the software module 406 to perform the functionality of the software module 406. For example, an admin user may use a user interface to enter information about software applications into the platform 204, download the software applications, configure a virtual machine 416 to execute the software applications, or other functionality.

FIG. 7A depicts one embodiment of a table 700. The table 700 may be stored in the database 414. The table 700 may store information related to the software applications maintained by the software module 406. In some embodiments, the table 700 may include an entity 702. The entity 702 may include an entity associated with an entity system 102. The table 700 may include a software application 704. The software application 704 may include the name of a software application maintained by the software module 406. The table 700 may include a software application type 706. The type 706 may include a type of software that the software application 704 is. For example, as shown in FIG. 7A, the software application "Zoom" may be of the video conferencing type ("Video"), the software application "Citrix Workspace" may be of the desktop virtualization type ("DV"), and the software application "ThriveUX" may be of the EMR access type ("EMR").

The table 700 may include a version 708. The version 708 may indicate the version of the associated software application 704 that is compatible with the associated entity's 702 entity system 102. In some embodiments, different entities 702 may use different versions 708 of the same software application 704. For example, as depicted in FIG. 7A, the first row and the third row the table 700 indicate that both the entities 702 "Boston Medical Center" and "Shriner's Hospital" use the software application 704 "Zoom," but the entities 702 use different versions 708 of the "Zoom" software application 704.

In some embodiments, the platform 204 may include the entity module 408. The entity module 408 may maintain entity data. Entity data may include data about one or more entities that own, operate, or maintain the one or more entity systems 102(1)-(n). The entity data may be stored in the database 414. In one or more embodiments, an admin user may use the entity module 408 to perform the functionality of the entity module 408.

In some embodiments, the entity module 408 may receive selection data. The selection data may be from the software application 202, which may have sent the selection data to the platform 204. The selection data may include an entity identifier. The entity identifier may include data that may identify, on the platform 204 or the database 414, an entity system 102. The entity module 408 may retrieve entity data from the database 414. The retrieval of the entity data may be based on the entity identifier. The entity module 408 may send at least a portion of the entity data to the client software application 202.

In one embodiment, the entity data may include text data. The entity data may include a category and one or more corresponding values for that category regarding an entity. A category may include a nursing station, a call schedule, information technology contact information, handoff information, or test or treatment information. A category may include general information, frequently used contact information, medical worker duties, software application information, workflow information, guidelines and procedures information, shift information, medical facility technology information, or other categories. Each category may include corresponding values. For example, the frequently used contact information may include one or more telephone numbers for the specific entity that the entity data concerns. In one embodiment, a value may include a hyperlink. In some embodiments, a category may include one or more subcategories. For example, the medical worker duties category may include a surgeon duties subcategory, an emergency room physician duties subcategory, a nurse duties subcategory, etc.

In one embodiment, the entity module 408 may receive selection data from the client software application 202 being used by an admin user. The selection data may include an entity identifier. The entity module 408 may receive first entity data from the client software application 202. The entity module 408 may update, based on the first entity data and the entity identifier, the database 414. The entity data may include a new or updated category, a new or updated subcategory, new or updated values for a category or subcategory, or data indicating to the database to delete a category, subcategory, or a value. In some embodiments, a category may include a default category or a custom category. A default category may include a category that cannot be deleted, and a custom category may include a category that can be deleted.

In some embodiments, an admin user may generate at least a portion of the entity data. An admin user may generate the entity data using a user interface (e.g., a webpage) with text fields where the admin user can input the entity data. The admin user may generate the categories or subcategories and may fill in the values corresponding to those categories or subcategories. The admin user may modify or delete entity data (e.g., in response to an entity's information changing). In some embodiments, only an admin user may generate or modify entity data. In some embodiments, a remote worker user may send information to an admin user (e.g., via email, an internal messaging service of the platform 204, or webpage that accepts remote worker user feedback) so that an admin user can update the entity data.

In some embodiments, the entity module 408 may add a new database entry to the database 414 based on the first entity data. In some embodiments, the entity module 408 may update a database entry of the database 414 based on the first entity data. The entity module 408 may delete a database entry of the database 414 based on the first entity data.

The entity data may include a name, contact information, location information, or other information regarding the entity. The data may include the software applications used by the entity's entity system 102. The data may include other data associated with the entity systems 102(1)-(n).

Figure 7B:
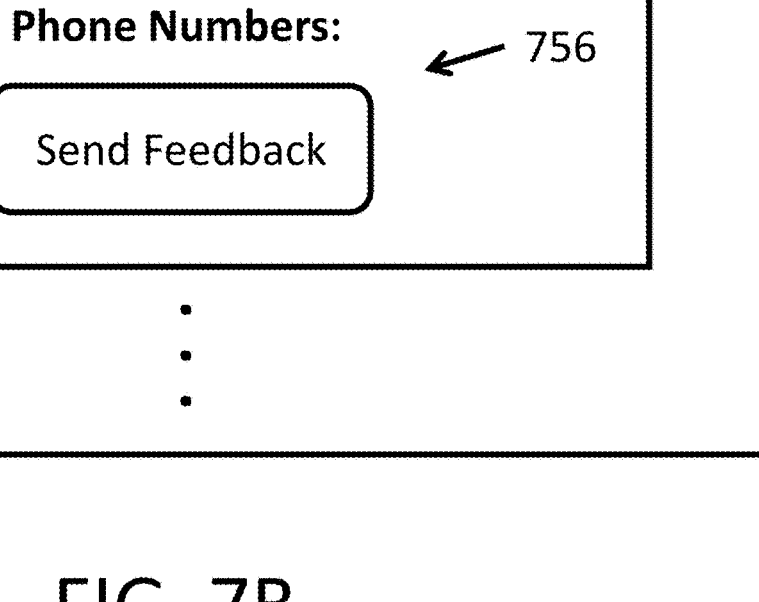
FIG. 7B is a front view illustrating one embodiment of a user interface of a software application of a user device for a system of automating processes for remote work.

FIG. 7B depicts one embodiment of a user interface 750. The user interface 750 may include a user interface for displaying entity data. The user interface 750 may include a facility 752. The facility 752 may include text data indicating the facility to which the entity data pertains. The user interface 750 may include one or more categories 754. The categories may include a nursing station, a call schedule, information technology contact information, handoff information, or test or treatment information. The user interface 750 may include further categories 756. The categories 756 may include general information, frequently used contact information, medical worker duties, software application information, workflow information, guidelines and procedures information, shift information, medical facility technology information, or other categories. A category 756 may include a button to view the values corresponding to the category 756 or to view subcategories corresponding to the category 756. The category 756 may include a button to send feedback regarding the entity data to an administrative user.

In one embodiment, the platform 204 may include a load balancing module 410. The load balancing module 410 may distribute virtual machine 416 execution, software application execution, application tasks or threads, or other computer functionality among the computing resources of the platform 204. The computing resources may include the one or more computing devices of the platform 204, the database 414, the one or more virtual machines 416, or other computing resources. The load balancing module 410 may distribute the functionality among the computing resources to increase efficiency of the platform 204, decrease response time, or avoid overloading certain computing resources while other resources are idle. In some embodiments, an admin user may use the load balancing module 410 to configure the load balancing functionality.

In one embodiment, the platform 204 may include a robotic process automation (RPA) module 412. The RPA module 412 may be configured to automate certain tasks for the user of the user device 104 when remotely interacting with the platform 204. The RPA module 412 may automate these tasks by sending input commands to the remote computing environment as if those input commands had come from the user.

As an example of the functionality of the RPA module 412, after a user has logged into the platform 204, the platform 204 may display, via the software application 202, a virtualized desktop whose applications execute on the platform 204. The virtualized desktop may include an icon that launches a video conferencing application that requires login information. Instead of the user clicking on the icon to launch the video conferencing application, waiting for the application to open, and inputting his or her login information into the application, the RPA module 412 may, in response to detecting that the user has clicked on the application's icon, detect when the application has opened, retrieve the user's login information (e.g., from the account module 404), and send virtualized keystroke commands to the application to automatically enter the user's retrieved login information into the application.

In one embodiment, the platform 204 may include one or more virtual machines 416. A virtual machine 416 may include a virtualization or emulation of a computing device. The virtual machine 416 may include software applications installed on the virtual machine 416. The virtual machine 416 may include data stored on the virtual machine 416. In some embodiments, a virtual machine 416 may receive software applications from the software module 408 to be installed on or execute on the virtual machine 416. For example, prior to the initialization of the virtual machine 416, the software module 408 may configure the virtual machine 416 to initialize with selected versions of selected software applications installed on the virtual machine 416. In some embodiments, the virtual machine 416 may include a virtualized desktop where applications execute and whose display information is sent to the software application 202 of the user device 104.

Figure 8:
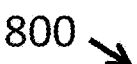
FIG. 8 is a front view illustrating one embodiment of a user interface of a software application of a user device for a system of automating processes for remote work.

FIG. 8 depicts one embodiment of a user interface 800. The user interface 800 may include a user interface displayed on the user device 104. The user interface 800 may include a user interface of the software application 202. The user interface 800 may include a virtualized desktop of the platform 204. The software application 202 may display the user interface 800 in response to the remote worker user logging into the platform 204 (e.g., after logging in using the functionality described above in relation to FIG. 3A and FIG. 3B).

The user interface 800 may include a menu 802. The menu 802 may include menu options that the remote worker user may use to operate on the platform 204. Example menu items may include a menu item for requesting support from an admin user of the platform 204 (discussed further below), logging out of the platform 204, or other functionality. The user interface 800 may include a messaging icon 804. In response to the remote worker user interacting with the messaging icon 804, the user interface 800 may display one or more messages that the remote worker user has sent or received. The messages may include messages on an internal messaging service of the platform 204, email messages, SMS messages, or some other type of messages. The platform 204 may send the messages to the user device 104 to be displayed on the user interface 800 of the software application 202. The user interface 800 may include a platform user account icon 806. In response to the remote worker user interacting with the platform user account icon 806, the user interface 800 may display one or more options associated with the remote worker user's platform user account. The options may include the option to update the remote worker user's platform user account information (which may include information included in the table 500 of FIG. 5), log out of the platform 204, or other platform user account functionality.

The user interface 800 may include a platform application selection area 808. The platform application selection area 808 may include one or more platform application icons 810(1)-(*n*). Each platform application icon 810 may correspond to a platform application that the remote worker user may use to effect operations on the platform 204. In some embodiments, a platform application may not include a separate software application from the platform 204 but may include a portion of the functionality of the platform 204 or its modules. In one embodiment, a platform application may include an entity applications selection application, a speech-to-text application, a clinical activity logging application, or other applications, all of which are further discussed below.

Figure 9A:
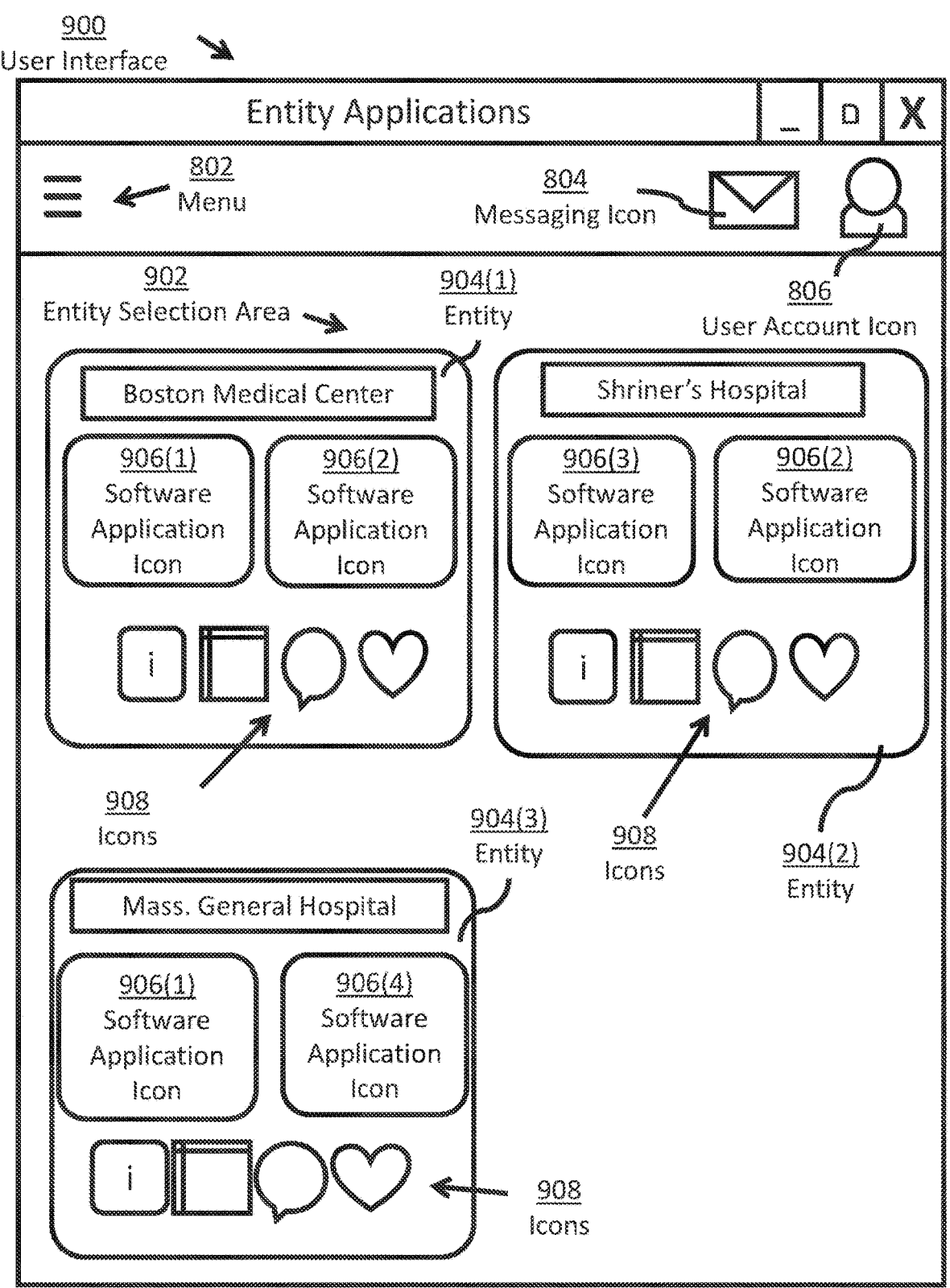
FIG. 9A is a front view illustrating one embodiment of a user interface of a software application of a user device for a system of automating processes for remote work.

FIG. 9A depicts one embodiment of a user interface 900. The user interface 900 may include a user interface displayed on the user device 104. The user interface may include a user interface of the software application 202. The user interface 900 may include a virtualized desktop of the platform 204. The software application 202 may display the user interface 900 in response to the remote worker user logging into the platform (e.g., after logging in using the functionality described above in relation to FIG. 3A and FIG. 3B). The software application 202 may display the user interface 900 in response to the remote worker user selecting the entity applications selection application icon 810 of the platform application selection area 808 of the user interface 800 of FIG. 8. In some embodiments, the user interface 800 may include the menu 802, the messaging icon 804, or the platform user account icon 806. The menu 802 may include a menu item configured to return the remote worker user to the user interface 800 of the FIG. 8.

The user interface 900 may include an entity selection area 902. The entity selection area 902 may include a group of entities 904(1)-(*n*), and each entity 904 may correspond to an entity system 102 that the remote worker user of the user device 104 may connect to. Which entities 904 appear in the entity selection area 902 may be determined by the account module 404. In some embodiments, as depicted in FIG. 9A, the entity selection area 902 may include a grid of entities 904 that a remote worker user may interact with by clicking, tapping, or otherwise. In some embodiments, the entity selection area 902 may include a drop-down box where a remote worker user may select the desired entity system 102 to connect to, or may include another user interface component.

Each entity 904 may include one or more software applications icons 906(1)-(*n*). Each software application icon 906 may correspond to a software application that may be compatible with the entity system selected in the entity selection area 902. Which software applications are compatible with the selected entity system 102 may be determined by the software module 406. Each entity 904 may include one or more icons 908. An icon may include functionality of the platform 204 related to the entity 904. An icon may include an icon to display entity data, an icon to execute clinical activity logging, an icon to execute automated support, or other functionality.

Figure 9B:
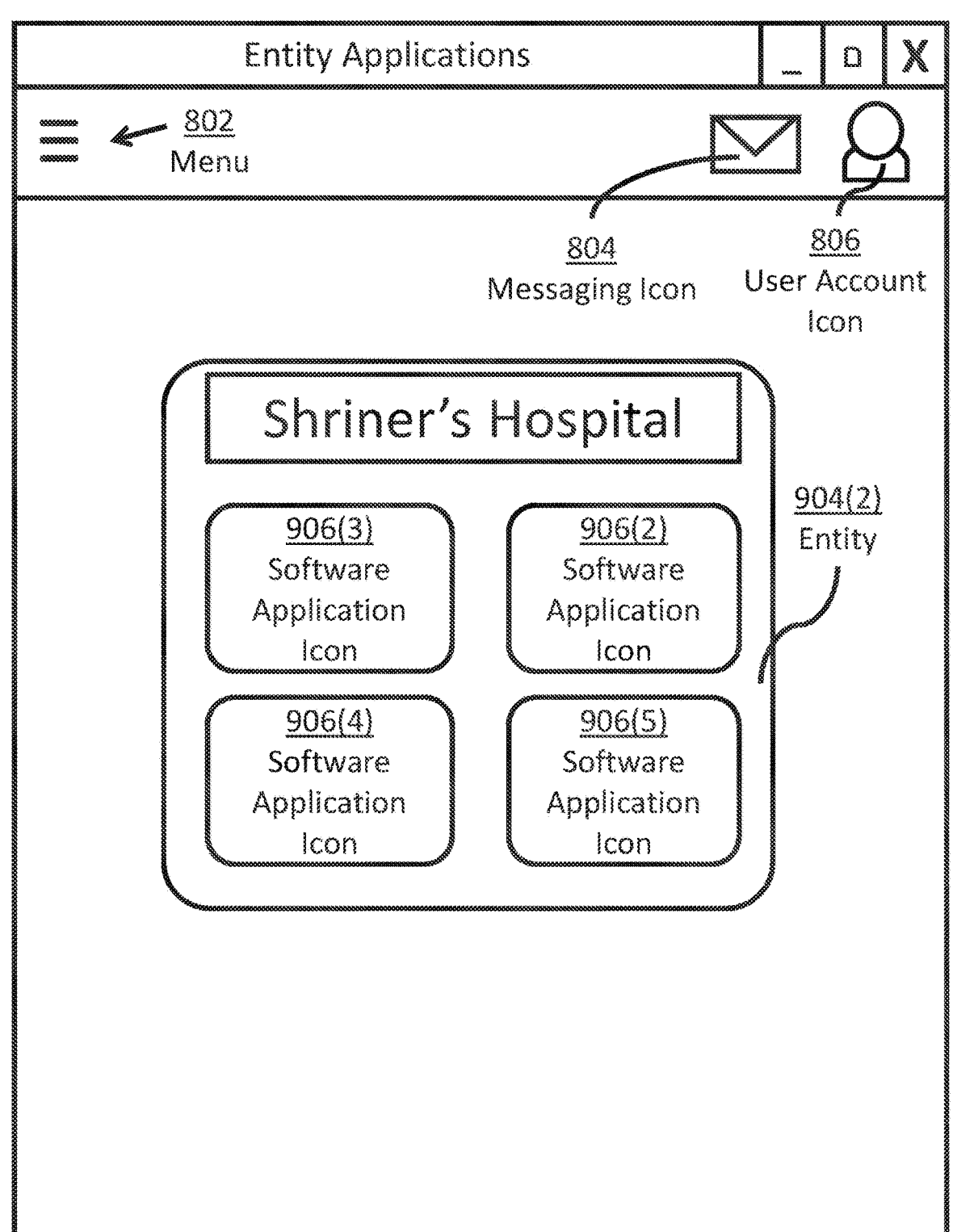
FIG. 9B is a front view illustrating another embodiment of a user interface of a software application of a user device for a system of automating processes for remote work.

FIG. 9B depicts one embodiment of the user interface 900. The user interface 900 may be displayed, as depicted in FIG. 9B, in response to a remote worker user interacting with an entity 904. The user interface 900 may include an expanded version of an entity 904. The expanded version of the entity 904 may include all available software application icons 906(1)-(*n*) that are available to the remote worker user for that entity 904.

A remote worker user of the software application 202 may interact with a software application icon 906 (e.g., by clicking on the icon 906 or touching the icon on a touchscreen) via the user interface 900 to launch the corresponding software application. The software application may execute on the platform 204 remotely. As discussed above, in some embodiments, the RPA module 412 may detect the launching of the application and may perform one or more automated tasks regarding the software application to assist the user.

In one embodiment, the software application 202 may include speech-to-text functionality. The software application 202 may detect a selection, from the remote worker user, of a speech-to-text button on a user interface. The user interface may include a user interface of the software application 202. The software application 202 may open, on the user interface, a textbox configured to contain text data. The software application 202 may receive audio data from a microphone. The microphone may include a microphone of the user device 104 and may be in data communication with a processor of the user device 104. The software application 202 may generate text data based on the audio data. The text data may correspond to content of the audio data. The software application 202 may display the text data in the textbox of the user interface.

The remote worker user may activate the speech to text functionality by interacting with a platform application icon 810 of the user interface 800. The speech-to-text functionality may receive audio data and process the audio data into computer-readable text data. The speech-to-text functionality may include natural language processing (NLP), machine learning, or other functionality that may generate text data based on the received audio data. The speech-to-text functionality may send the generated text data to a pre-determined location. The pre-determined location may include a file stored on the user device 104 or the platform 204, a textbox of the user interface of the software program 202 (e.g., a notes section, an EMR currently open and displayed on the software application 2020, etc.), or in some other location. In some embodiments, the remote worker user may interact with the software application 202 to pause or resume the speech-to-text functionality. In some embodiments where the software application 202 includes a web browser, a browser plugin may include the speech-to-text functionality.

Figure 11:
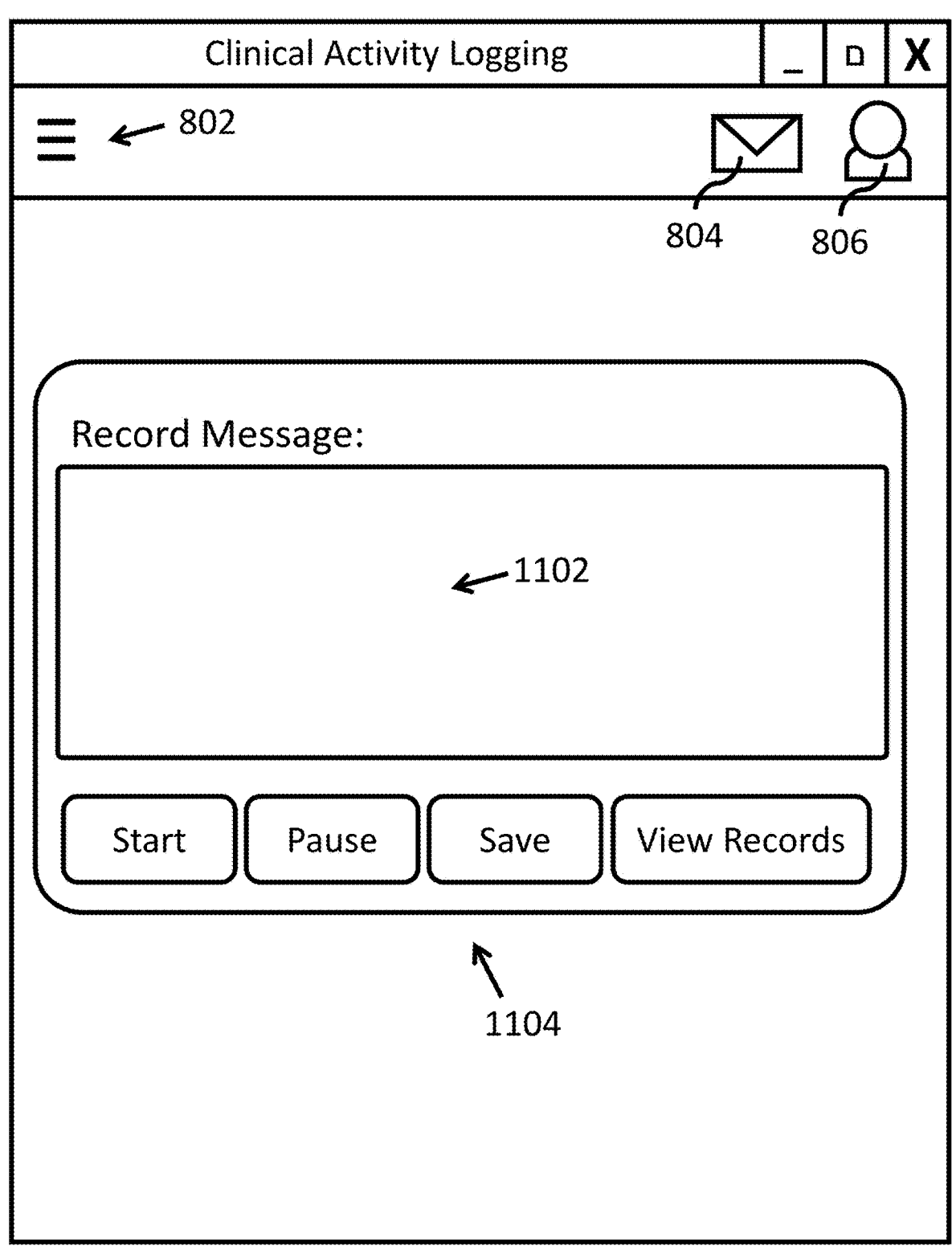
FIG. 11 is a front view illustrating one embodiment of a user interface of a software application of a user device for a system of automating processes for remote work.

FIG. 11 depicts one embodiment of a user interface 1100. The user interface 1100 may include a speech-to-text user interface. The user interface 1100 may include certain components of the user interface 800 of FIG. 8 (such as the menu 802, the messaging icon 804, or the platform user account icon 806). The user interface 1100 may include a textbox 1102. The textbox 1102 may include the text data generated from the audio data. The text data in the textbox 1102 may be selectable so that it can be copied and pasted to other portions of the software application 202 or to other software applications. The user interface 1100 may include one or more buttons 1104. The buttons may include a start recording button, a pause recording button, a save button, or a view records button, whose functionalities have been explained above.

In some embodiments, the software application 202 may store the audio data in a data storage of the user device 104. The data storage may include a hard drive disk, a solid-state drive, a memory (such as random access memory, a flash memory, or some other type of memory). In one embodiment, the software application 202 may isolate a portion of the audio data, select one or more text characters from a dictionary stored on the user device 104 based on the isolated portion of the audio data, and include the selected one or more text characters in the text data. The dictionary may include a map of portions of audio data to corresponding one or more text characters.

In some embodiments, the software application 202 may detect one or more keyboard inputs (or other user inputs such as a touchscreen input) and update the text data in the textbox of the user interface based on the one or more detected keyboard inputs. This may allow the remote worker user to correct errors or make additions to the generated text data. In some embodiments, the remote worker user may copy at least some of the text data to a virtual clipboard and paste the copied text data to another location. The other location may include a portion of the software application 202 or another software application of the user device 104. The other location may include an EMR user interface, an electronic fax user interface, or some other location or software application.

In one or more embodiments, the software application 202 may include remote worker support functionality, sometimes called "automated support." Remote worker support functionality may include multiple types of support. Types of support may include provider support, information technology support, and non-emergency support. In some embodiments, provider support may include a remote worker user (such as a medical provider) providing support to another remote worker user (who may also be a medical provider). Provider support may include the platform 204 receiving first login data from a client software application 202 executing on a first user device 102 of a first remote worker user. The remote worker user may include a medical provider user. The platform 204 may authenticate the first remote worker user based on the first login data. The platform 204 may receive, from the client software application 202, a provider support data packet. The provider support data packet may include text data. The platform 204 may generating a second data packet. The second data packet may include the text data. The platform 204 may send the second data packet to a second user device 104 of a second remote worker user. The second remote worker user may include a medical provider user.

Information technology support may include an admin user providing assistance to the remote worker user. The admin user may include an admin user of the platform 204 and may provide assistance to the remote worker user regarding the platform 204 or its functionality or the functionality of its modules 402-412. In one embodiment, information technology support may include a support user of an entity system 102 providing assistance to the remote worker user. This may include the support user of the entity system 102 providing assistance to the remote worker user regarding a software program used on the entity system 102. In some embodiments, the platform 204 and an entity system 102 may be owned, operated, or controlled by different entities, and, thus, it may be more efficient for a support user to provider assistance regarding a software program used on the entity system 102 instead of an admin user of the platform 204. The platform 204 may receive, from the client software application 202, an information technology support data packet. The information technology support data packet may include a help ticket. The help ticket may include first text data indicating a subject of the help ticket, and second text data indicating a description of the help ticket. The platform 204 may generate a second data packet. The second data packet may include the first text data and the second text data. The platform 204 may send the second data packet to an administrative user.

In one or more embodiments, the remote worker support functionality may include the remote worker user interacting with a portion of the user interface 800 of the FIG. 8. The portion of the user interface 800 may include a menu item (such as the menu icon 802) (e.g., clicking or tapping on a "Help" menu item), a platform application icon 810, an icon 908 of an entity 904 of the user interface 900, or some other portion of the user interface 800 or 900. In response, the software application 202 may send data to the platform 204 or the entity system 102 (e.g., in the form of a provider support data packet or an information support data packet) indicating that the remote worker user has requested support. In response, the platform 204 or the entity system 102 may send notification data to another remote worker user, an admin user, or a support user. The notification data may include an SMS message to the receiving user's user device 104, a message of an internal messaging service of the platform 204 or the entity system 102, an email, a help ticket in an issue tracking system associated with the platform 204 or the entity system 102, a message sent through an API, etc. The notification may include a secured messaging text populated on a secured texting platform of the platform 204 or an external service in data communication with the platform 204. The notification data may include contact information of the remote worker user that requested support (e.g., as retrieved by the database 414 or the account module 404 of the platform 204 or a database or data storage of the entity system 102). The receiving user may use the notification data to contact the remote worker user. The receiving user may use a remote access or remote control software application on the his or her user device 104 to view or control the remote worker user's user device 104 to assist the remote worker user. In some embodiments, the remote worker support functionality may include providing contact information for the receiving user to the remote worker user (e.g., as retrieved by the account module 404 or the entity module 406 from the database 414).

In some embodiments, remote worker support functionality may include other remote worker users providing assistance to a remote worker user. The remote worker support functionality may include the remote worker user interacting with a menu item (such as the menu icon 802) on the user interface 800 of the remote worker user's software application 202, and in response, the user interface 800 may display a list of other remote worker users. The software application 202 may receive the list from the platform 204, the entity system 102, or some other location. The software application 202, the platform 204, or the entity system 102 may filter the list based on one or more criteria. The criteria may include that the other remote worker users (1) work at the same entity or at a selected entity, (2) are currently on duty, (3) include the same role as the requesting worker remote user, or (4) other criteria. The requesting remote worker user may select, on the user interface 900, which other remote worker users from the list he or she would like to contact for support. The software application 202 may send data to the platform 204 or the entity system 102 indicating which remote worker users the requesting remote worker users selected. The platform 204 or the entity system 102 may receive the data, and in response, may retrieve contact information for the selected remote worker users (e.g., using the account module 404, the database 414, or a data storage of the entity system 102) to contact the selected remote worker users. Contacting the selected remote worker users may include placing the requesting remote worker user and the selected remote worker users in a group SMS message session, a group message session of an internal messaging service of the platform 204 or the entity system 102, a group email chain, or some other group messaging service.

FIG. 12A depicts one embodiment of a user interface 1200. The user interface 1200 may include a user interface for remote worker support functionality. The user interface 1200 may include certain components of the user interface 800 of FIG. 8 (such as the menu 802, the messaging icon 804, or the platform user account icon 806). The user interface 1200 may include a schedule type 1202. The schedule type 1202 may include text data indicating the type of schedule the remote worker user is on. The schedule type 1202 may include a textbox, drop-down box, or other component. The user interface 1200 may include an assistance type 1204. The assistance type 1204 may include text data indicating the type of assistance the remote worker user is requesting. The assistance type 1204 may include a textbox, drop-down box, or other component. The user interface 1200 may include a subject 1206. The subject 1206 may include text data indicating the subject of the requested assistance. The user interface 1200 may include a description 1208. The description 1208 may include text data describing further details about the requested assistance. The subject 1206 or the description 1208 may include a textbox or other component. The user interface 1210 may include a "Submit" button 1210. The remote worker user interacting with the "Submit" button 1210 may generate a help ticket based on the data provided in the user interface 1200. The platform 204 or an entity system 102 may receive the help ticket and may route it to the appropriate entity system.

In one embodiment, an admin user may use a user interface to view one or more submitted help tickets. The admin user may filter or sort the help tickets by entity, date, type of assistance, status, or other criteria. The user interface may display to the admin user the subject 1206 and the description 1208 associated with the help ticket.

In some embodiments, the RPA module 412 or the RPA functionality of the software application 202 may perform functionality in addition to or alternative from logging the remote worker user into a selected software application. In one embodiment, the RPA module 412 or the RPA functionality may create an account for a remote worker user for a selected software application. The RPA module 412 or the RPA functionality may retrieve information about the remote worker user in order to create the account. As an example, the software application 202 may launch a video conferencing software application (either in a virtual machine 416 or on the user device 104). The remote worker user may not have an account for the video conferencing software application. The RPA module 412 or the RPA functionality may select an icon or link on the video conferencing software application (e.g., on a login screen) to create a new account. The RPA module 412 or the RPA functionality may retrieve remote worker user information (e.g., from the table 500 of the FIG. 5) and fill in the account creation information using the retrieved information. The RPA module 412 or the RPA functionality may generate a username or password for the remote worker user and store them in the database 414 (e.g., in the table 600 of the FIG. 6).

Figure 10:
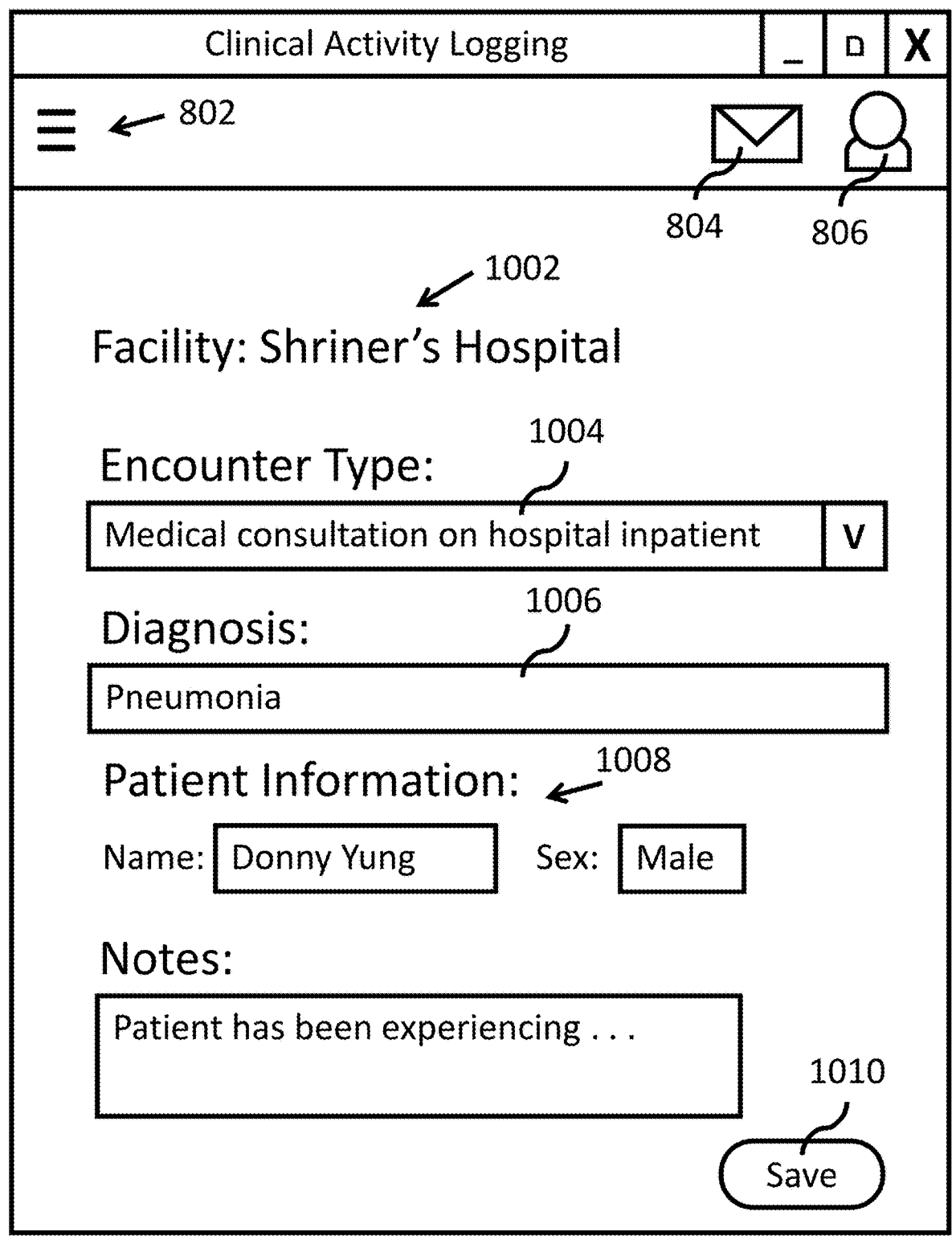
FIG. 10 is a front view illustrating one embodiment of a user interface of a software application of a user device for a system of automating processes for remote work.

FIG. 10 depicts one embodiment of a user interface 1000. The user interface 1000 may include a user interface of the software application 202. The user interface 1000 may include a user interface of a clinical activity logging application of the platform 204. The user interface 1000 may launch in response to the remote worker user interacting with a corresponding platform application icon 810 of the user interface 800 of the FIG. 8 or an icon 908 of an entity 904 of the user interface 900 of the FIG. 9A. In some embodiments, the user interface 1000 may include the menu 802, the messaging icon 804, or the platform user account icon 806. The menu 802 may include a menu item configured to return the software application 202 to the user interface 800.

In one embodiment, the remote worker user may include a medical worker. The user interface 1000 may include a user interface for the medical worker to enter clinical information in order for the information to be saved to the platform 204 and utilized by other modules of the platform 204. The user interface 1000 may include a facility name 1002. The facility name 1002 may include a textbox indicating the facility associated with the clinical information the medical worker is inputting.

The user interface 1000 may include an encounter selection 1004. The encounter selection 1004 may include a textbox, dropdown menu, or other menu for inputting the encounter type associated with the clinical information the medical worker is inputting. Example encounter selection 1004 options may include a medical consultation on a hospital inpatient, initial hospital visit, new patient consultation, emergency department visit, or other encounter types. The user interface 1000 may include an diagnosis selection 1006. The diagnosis selection 1006 may include a textbox, dropdown menu, or other menu for inputting the diagnosis associated with the clinical information the medical worker is inputting.

In some embodiments, the user interface 1000 may include a patient information input area 1008. The patient information input area 1008 may include a textbox, dropdown menu, or other menu for inputting patient information associated with the clinical information the medical worker is inputting. The patient information may include the patient's name, demographic information, a medical code (such as a Current Procedural Terminology (CPT) code, a electroencephalography (EEG) code, an International Statistical Classification of Diseases and Related Health Problems (ICD) code), or other patient information. The user interface 1000 may include input areas for other information related to the clinical information such as notes, a time or date of the encounter, a length of the encounter, or other information. The user interface 1000 may include a save button 1010 or other component. In response to the worker interacting with the save button 1010 or other component, the platform 204 may generate a clinical activity log entry and store the clinical activity log entry on the platform 204 (e.g., in the database 414).

In one embodiment, the software application 202 may generate the clinical activity log entry on the user device 104. The software application 202 may encrypt the log entry and transmit it to the platform 204. In other embodiments, the user interface 1000 may include a user interface of a software application executing on the platform 204 and whose display data is received by the software application 202 running on the user device 104 (e.g., using desktop virtualization, a remote desktop software application, etc.).

In some embodiments, the user interface 1000 may display one or more clinical activity log entries for the medical worker to view. The one or more clinical log entries may be filterable by the medical worker that created the log entry, the facility or entity associated with the log entry, a time or date the log entry was created, or by other criteria associated with clinical log entries. In some embodiments, a medical worker may use the clinical activity log displayed on the user interface 1000 to open a previous log entry and edit the contents of the log entry. The software application 202 or the platform 204 may limit the medical worker's ability to edit log entries to log entries created by that medical worker user.

In one or more embodiments, an admin user may use the user interface 1000 on the admin user's user device 104 to view one or more clinical activity logs. The admin user may filter the one or more clinical log entries using similar functionality to the filtering performed by the medical worker user as discussed above. The admin user may also be able to open a previous log entry and edit the contents of the log entry. The admin user may be able to edit a log entry of any medical worker user or only a pre-determined group of medical worker users. In some embodiments, the platform 204 may include one or more users whose type may include a clinical log user. A clinical log user may be configured to perform the same or similar clinical activity log functions as the admin user, but may not be configured to perform other admin user functionality (e.g., onboarding a medical worker user).

In one embodiment, a medical worker user, admin user, or clinical log user may be able to generate a report of one or more clinical activity log entries. The user generating the report may select which log entries the platform 204 includes in the report. The user may filter the log entries as discussed above. Generating the report may include the platform 204 generating a file that includes the log entries included in the report. The file may include a portable data format (PDF) file, a spreadsheet file (e.g., a comma-separated values (CSV) file, a MICROSOFT EXCEL file, etc.), or some other file format.

In some embodiments, a billing or payroll software applications may receive data from the clinical activity log entries. The billing or payroll software applications may be stored or may execute on the platform 204 or one or more of the entity systems 102(1)-(n). The billing or payroll software applications may receive the data via an API of the platform 204. The billing or payroll software applications may use the received data to automatically generate invoices, medical claims, or other documents.

In some embodiments, the clinical activity log entry functionality may assist with compliance with privacy laws or regulations. In some embodiments, since the user accesses the clinical activity log entries remotely (e.g., via desktop virtualization, remote desktop, or a web browser), patient data or other protected data may not be stored on the user device 104. Furthermore, the data communication between the user device 104 and the platform 204 or an entity system 102 may be encrypted, which also assists with legal and regulation compliance.

In one embodiment, the platform 204 may use data from one or more clinical activity log entries to report one or more key metrics. The platform 204 may generate a file that may include a report of the one or more key metrics. In some embodiments, an entity that operates the platform 204 and one or more entities that operate the one or more entities systems 102(1)-(n) may select the one or more key metrics. One or more key metrics may help identify performance information or data that may help improve the operations of the entity operating the platform 204 or one or more entities operating the entity systems 102(1)-(n).

It should be noted that while certain database tables (e.g., the table 500 of FIG. 5 or the table 600 of FIG. 6) have been described as relational tables, the tables or the information stored therein may be stored in some other type of database storage structure. In some embodiments, the data sent between the user device 104 and the platform 204 may be encrypted. The encryption may include secure sockets layer—(SSL) or Health Insurance Portability and Accountability Act—(HIPAA) compliant encryption.

Figure 13:
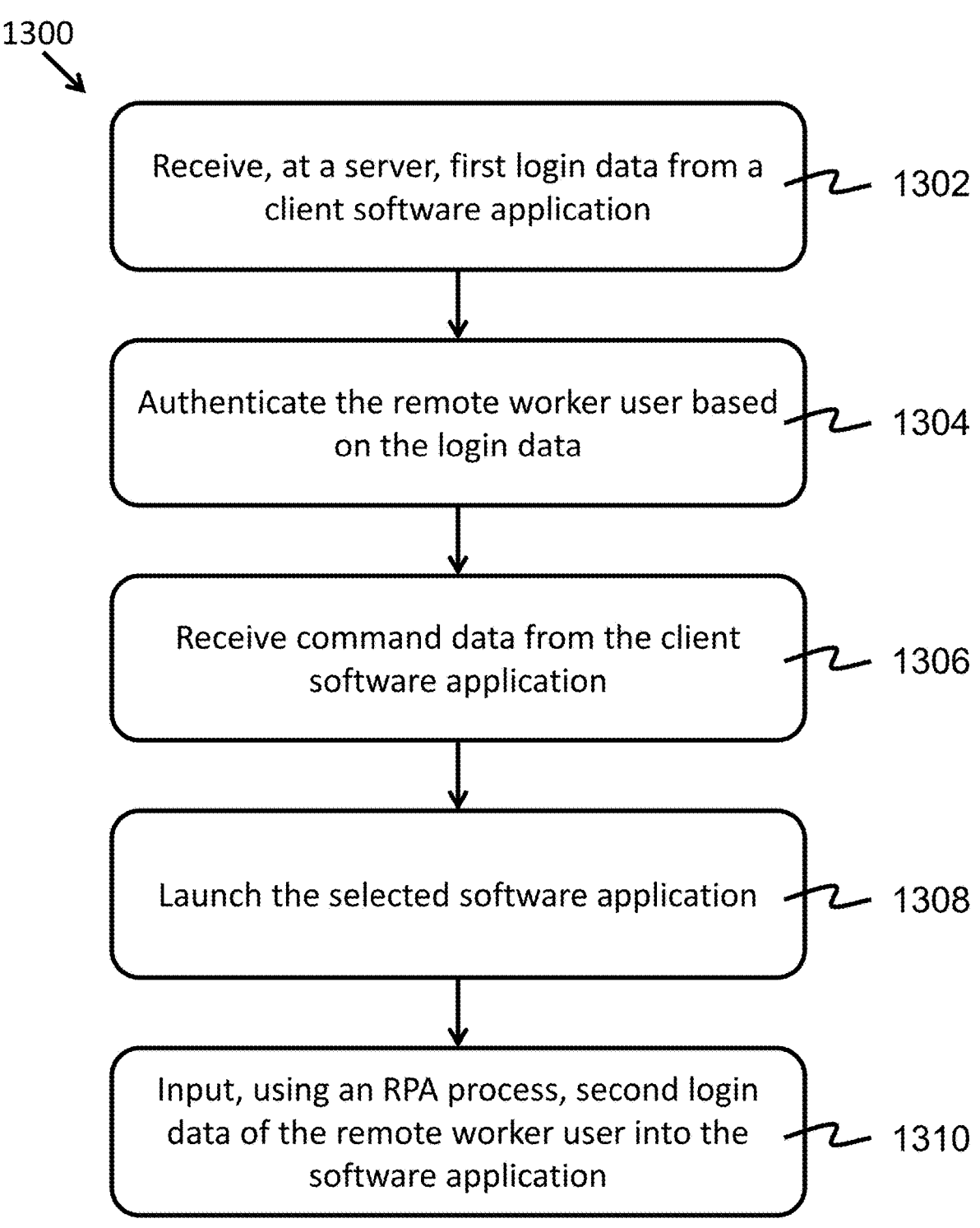
FIG. 13 is a flowchart illustrating one embodiment of a method of automating processes for remote work.

FIG. 13 depicts one embodiment of a method 1300. The method 1300 may include a method of automating processes for remote work. The method 1300 may include receiving 1302, at a server, first login data from a client software application. The client software application may be executing on a user device of a remote worker user. The method 1300 may include authenticating 1304 the remote worker user based on the first login data. The method 1300 may include receiving 1306, at the server, command data from the client software application. The command data may include data indicating to the server to launch a software application. The method 1300 may include launching 1308, on the server, the software application. The method 1300 may include inputting 1310, using an RPA process, second login data of the remote worker user into the software application.

In some embodiments, the server may include a server hosting at least a portion of the platform 204. The client software application of step 1302 may include the software application 202 of the user device 104. In some embodiments, the first login data of the steps 1302 or 1304 may include may include one or more authentication factors (e.g., a username, a password hash, a PIN, a biometric authentication factor). In one embodiment, receiving 1302, at the server, the first login data may include the remote access module 402 of the platform 204 of FIG. 2 receiving the first login data. The remote access module 402 may send the first login data to the account module 404.

In one embodiment, receiving 1302 the first login data may include receiving a first portion of the first login data and a second portion of the first login data. The first portion may include the username and password hash of the remote worker user's platform user account. The second portion of the first login data may include an additional authentication factor. The additional authentication factor may include a PIN, an OTP, a biometric factor, or some other type of additional authentication factor. Receiving the additional authentication factor may include receiving the authentication factor from an external source. For example, the platform 204, in response to authenticating the remote worker user using the username and password hash, may send a notification to a MFA application on the user device 104 (which may include an application separate from the software application 202), and the remote worker user may need to confirm in the MFA application that the remote worker user is, in fact, attempting to log into the platform 204.

In some embodiments, the remote worker user may include the remote worker user of the user device 104. In one embodiment, authenticating 1304 the remote worker user may include the platform 204 authenticating the remote worker user. The platform 204 authenticating the remote worker user may include the account module 404 receiving the first login data from the remote access module 402. Authenticating 1304 the remote worker user may include a two-step process. In the first step, the account module 404 may query the table 500 based on the username of the first login data to determine if the password hash 504 stored in the table 500 of FIG. 5 matches the password hash of the first login data. If the two password hashes match, the two-step process may move to the second step. If the two password hashes do not match, the accounts module 404 may notify the remote access module 402, and the remote access module 402 may send a notification to the software application 202 notifying the remote worker user of the unsuccessful authentication.

In one or more embodiments, in the second step of the two-step authentication process, the platform 204 may prompt to remote worker user of the user device 104 to send an additional authentication factor to the platform 204. This may include the platform 204 sending a PIN to the remote worker user (e.g., via email or an SMS message), sending a notification to another service (e.g., a third party application on the user device 104) prompting the remote worker user to confirm the login attempt, sending a command to the software application 202 to perform a biometric scan (e.g., a fingerprint scan, a face scan, an eye scan) of the remote worker user, or the platform 204 may prompt for the additional authentication factor in another manner. The platform 204 may receive the additional authentication factor and send it to the account module 404. In response to the additional authentication factor authenticating the remote worker user, the account module 404 may log in the remote worker user to the platform 204.

In one embodiment, authenticating 1304 the remote worker user may include determining whether the remote worker user includes a predetermined role. For example, the accounts module 404 may determine whether the remote worker user is a medical worker, such as a physician, nurse, or other healthcare worker. The accounts module 404 may determine the remote worker user's role via the database 414 (e.g., as stored in the table 500 of the FIG. 5).

In some embodiments, the method 1300 may include the step of the platform 204 sending data indicating one or more entities to the software application 202 of the user device 104. The one or more entities may include the entities with which the remote worker user of the software application 202 is associated. The data indicating the one or more entities may be generated, populated, or otherwise constructed using data stored in the database 414 (e.g., the table 600 of FIG. 6). The each of the one or more entities may be associated with an entity system 102. In some embodiments, the software application 202 may display the one or more entities to the remote worker user. The software application 202 may display the one or more entities using a user interface, e.g., as depicted in the entity selection area 902 of FIG. 9A and FIG. 9B. In one embodiment, the data indicating the one or more entities may include display data (e.g., as part of a virtualized desktop) send to the software application 202. In some embodiments, data indicating the one or more entities may be stored on the software application 202, and software application 202 and the platform 204 may synchronize the data, e.g., in response to the remote worker user logging into the platform 204.

The remote worker user may use the software application 202 of the user device 104 to select an entity from the data indicating the one or more entities (e.g., using the user interface 900 of the FIG. 9A or FIG. 9B). In response, the software application 202 may send data indicating the selection of an entity by the remote worker user. The platform 204 may receive the data indicating the selection. In one or more embodiments, the method 1300 may include the step of the platform 204 sending data indicating one or more software applications to the software application 202 of the user device 104. The one or more software applications may include software applications associated with the selected entity. The data indicating the one or more software applications may be populated, generated, or otherwise constructed using the database 414 (e.g., using the table 700 of the FIG. 7A). The one or more software applications may include software applications that the entity system 102 of the selected entity uses or that are compatible with the entity system 102. In some embodiments, the software application 202 may display data indicating the one or more software applications to the remote worker user, e.g., as depicted in the entity application selection area 904 of FIG. 9A and FIG. 9B. In one embodiment, the data indicating the one or more software applications may include display data (e.g., as part of a virtualized desktop). In some embodiments, data indicating the one or more software applications may be stored on the software application 202, and software application 202 and the platform 204 may synchronize the list, e.g., in response to the remote worker user logging into the platform 204.

Using the software application 202, the remote worker user may select a software application from the one or more of software applications. The selected software application may include the software application the remote worker user wishes to launch. The software application may send a command to the platform 204 to launch the selected software application. In one embodiment, the step of receiving 1306 the command data from the software application 202 to launch the software application may include the remote access module 404 receiving the command data. In response, the platform 204 may perform the step of launching 1308 the selected software application.

Launching 1308 the selected software application may include a web-based launching. Using the web-based launching may occur in response to the software application 202 of the user device 104 including a web browser. In some embodiments of the web-based launching, the remote access module 402 may launch a virtual machine 416. The remote access module 402 may log into the virtual machine 416 using login credentials supplied by the accounts module 404. The login credentials may include login data from the table 500 of FIG. 5, the table 600 of FIG. 6, or from some other location in the database 414. The virtual machine 416 may include the selected software application installed on the virtual machine 416, which may include the version of the software application compatible with the selected entity system 102. The virtual machine 416 may launch the selected software application and execute the selected software application in the virtual machine 416 hosted on the platform 204. The virtual machine 416 may send output data to the remote access module 402, which may send the output data to the web browser of the user device 104. The output data may include display data, audio data, or other output from the software application or the virtual machine 416. The software application 202 of the user device 104 may display or reproduce the output data so that the remote worker user can interact with the selected software application running remotely on the virtual machine 416 of the platform 204.

Launching 1308 the selected software application may include a client-based launching. Using client-based launching may occur in response to the software application 202 including a desktop virtualization client, a remote desktop client, or some other non-web browser software application.

In some embodiments of the client-based launching, the software application 202 may determine whether the selected software application is installed on the user device 104 or whether the selected software application installed on the user device 104 is the correct version. In response to the software application 202 determining that the selected software application is installed on the user device 104 and is the correct version, the software application 202 may launch the selected software application on the user device 104. In response to the software application 202 determining that the selected software application is not installed on the user device 104 or that the selected software application installed on the user device 104 is the wrong version, the software application 202 may download and install the selected software application on the user device 104. For example, the software application 202 may download the selected software application from a digital distribution platform (e.g., the APPLE App Store or GOOGLE's Google Play) or some other location where the selected software application can be downloaded from. Once downloaded and installed, the software application 202 may launch the selected software application on the user device 104. In some embodiments, RPA functionality of the software application 202 may assist in downloading the selected software application or launching the selected software application.

In some embodiments of the client-based launching, the remote access module 402 may receive the command from the software application 202 and, in response, launch a virtual machine 416 on the platform 204. The remote access module 402 may log into the virtual machine 416 using login credentials supplied by the accounts module 404. The login credentials may include login data from the table 500 of FIG. 5, the table 600 of FIG. 6, or from some other location in the database 414. The virtual machine 416 may include the selected software application installed on the virtual machine, which may include the version of the software application compatible with the selected entity system 102. The virtual machine 416 may launch the selected software application. The virtual machine 416 may include a virtualized desktop that may be remotely controlled by the software application 202. The virtual machine 416 may send output data to the remote access module 402, which may send the output data to the software application 202 of the user device 104 so that the remote worker user can interact with the selected software application running remotely on the virtual machine 416 of the platform 204.

Step 1310 may include inputting 1310, using the RPA process, second login data into the software application that has been launched. The second login data may include a username (which may be different than the username of the first login data) and a password. Some embodiments of the web-based launching may include the RPA module 412 logging into the selected software application on the virtual machine 416. The RPA module 412 may receive the second login data for the selected software application from the account module 404 (e.g., from table 600 of FIG. 6 of the database 414). In some embodiments, other steps during the web-based launching may be performed by the RPA module 412. Such steps may include logging into the virtual machine 416, launching the selected software application in the virtual machine 416, or other operations.

Some embodiments of the client-based launching may include the software application 202 logging the remote worker user into the selected software application executing on the user device 104 (e.g., by retrieving the second login data stored on the user device 104 or retrieving the login credentials from the account module 404 of the platform 204). The software application 202 may include RPA functionality, which may carry out the logon functionality. Some embodiments of the client-based launching may include the RPA module 412 logging into the selected software application on the virtualized desktop of the virtual machine 416. The RPA module 412 may receive the second login data for the selected software application from the account module 404 (e.g., from table 600 of FIG. 6 of the database 414). In some embodiments, other steps during the web-based launching may be performed by the RPA module 412. Such steps may include logging into the virtual machine 416, launching the selected software application in the virtual machine 416, or other operations.

In some embodiments, the RPA process inputting 1310 the second login data may include the RPA process detecting the launch of the software application. The RPA process inputting 1310 the second login data may include the RPA process detecting a login user interface of the software application. For example, the RPA process may detect a textbox configured to receive a username and another textbox configured to receive a password. The RPA process inputting 1310 the second login data may include the RPA process sending virtualized input commands to the software application. The virtualized input commands may include a virtualized keystroke, a virtualized mouse click, a virtualized touchscreen interaction (e.g., a tap or a swipe), a virtualized audio input, or some other type of virtualized input command. The virtualized input command may include text characters of the second login data. For example, the RPA process may send a virtualized mouse click or a virtualized touchscreen tap to a username textbox of the software application to bring the username textbox into focus. Then, the RPA process may send a series of virtualized keystrokes or touchscreen taps to type the username of the second login data. The RPA process may perform similar steps to input the password of the second login data into the password textbox of the software application.

FIG. 14 depicts one embodiment of a method 1400. The method 1400 may include a method of automating processes for remote work. The method 1400 may include sending 1402, to a server, first login data of a remote worker user. The first login data may include a username and a password hash. The method 1400 may include receiving 1404, from the server, data indicating one or more entities and data indicating at least one software application associated with at least one entity of the one or more entities. The method 1400 may include displaying 1406, on a user interface, the at least one software application. The user interface may include a user interface of a software application 202 of a user device 104. The method 1400 may include launching 1408 the selected software application. The method 1400 may include inputting 1412, using a RPA process, second login data of the remote worker user into the selected software application. The method 1400 may include steps that may be similar to some of the steps of the method 1300 of FIG. 13.

In some embodiments, launching 1408 the selected software application may include launching the software application on the user device 104. In one or more embodiments, launching 1408 the selected software application may include launching the software application on the platform 204. In some embodiments, the software application may include a software application launched by a software application icon 906 or an icon 908.

Figure 15:
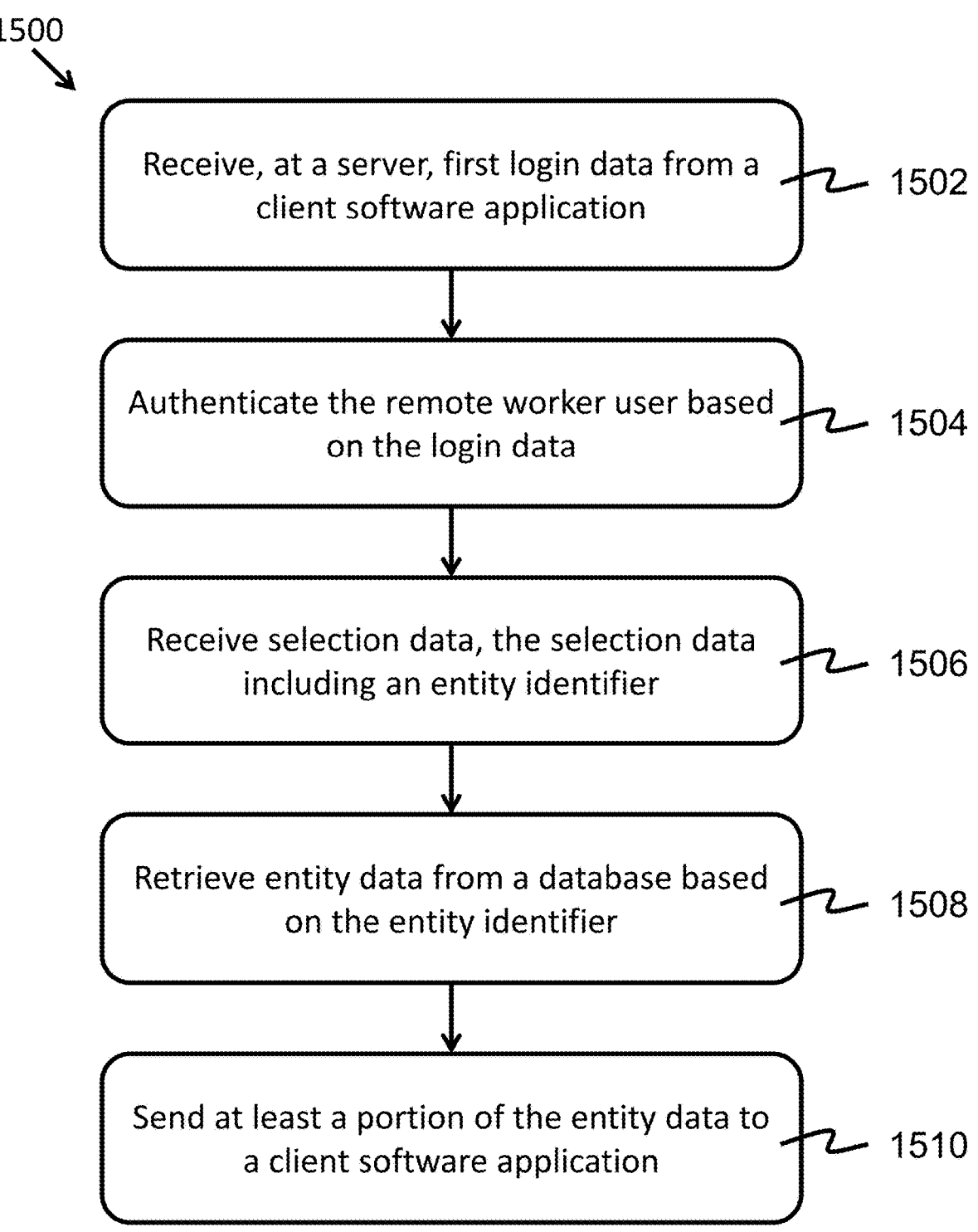
FIG. 15 is a flowchart illustrating one embodiment of a method of automating processes for remote work.

FIG. 15 depicts one embodiment of a method 1500. The method 1500 may include a method of automating processes for remote work. The method 1500 may include receiving 1502, at a server, first login data from a client software application executing on a user device of a remote worker user. The method 1500 may include authenticating 1504 the remote worker user based on the first login data. The method 1500 may include receiving 1506, at the server, selection data from the client software application. The selection data may include an entity identifier. The method 1500 may include retrieving 1508 entity data from a database in data communication with the server. The retrieval of the entity data may be based on the entity identifier. The method 1500 may include sending 1510 at least a portion of the entity data to the client software application.

Figure 16A:
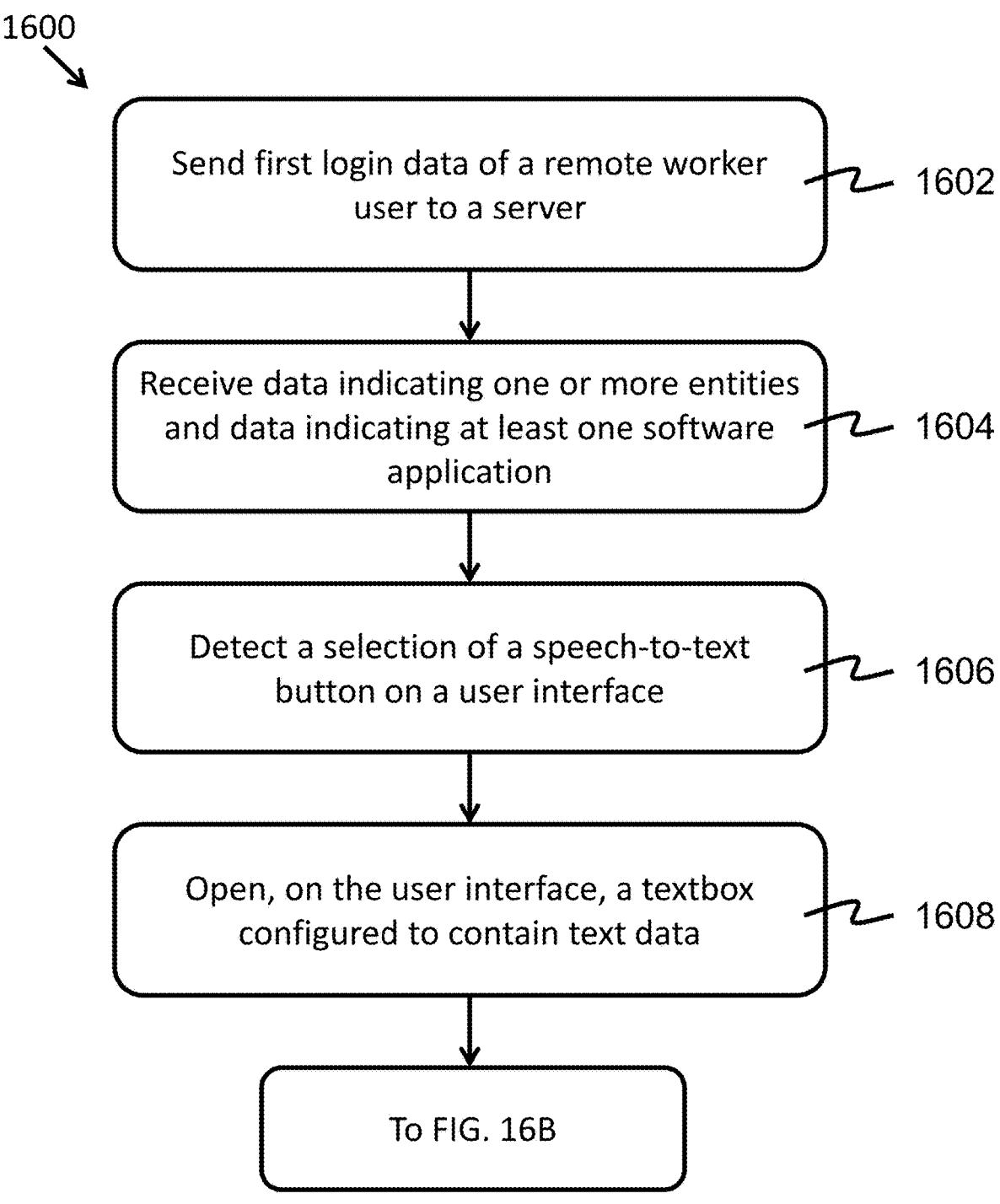
FIG. 16A is a flowchart illustrating one embodiment of a method of automating processes for remote work.

FIG. 16A and FIG. 16B depict one embodiment of a method 1600. The method 1600 may include a method of automating processes for remote work. The method 1600 include sending 1602, to a server, first login data of a remote worker user. The first login data may include a username and a password hash. The method 1600 may include receiving 1604, from the server, data indicating a plurality of entities and data indicating at least one software application associated with at least one entity of the plurality of entities. The method 1600 may include detecting 1606 a selection, from the remote worker user, of a speech-to-text button on a user interface. The method 1600 may include opening 1608, on the user interface, a textbox configured to contain text data. The method 1600 may include receiving 1610 audio data from a microphone in data communication with the processor. The method 1600 may include generating 1612 text data based on the audio data. The text data may correspond to content of the audio data. The method 1600 may include displaying 1614 the text data in the textbox of the user interface. In some embodiments, the method 1600 may include allowing the remote worker user to make edits to the text data or copy and paste portions of the text data to a software application, such as an electronic medical records database entry.

Figure 17:
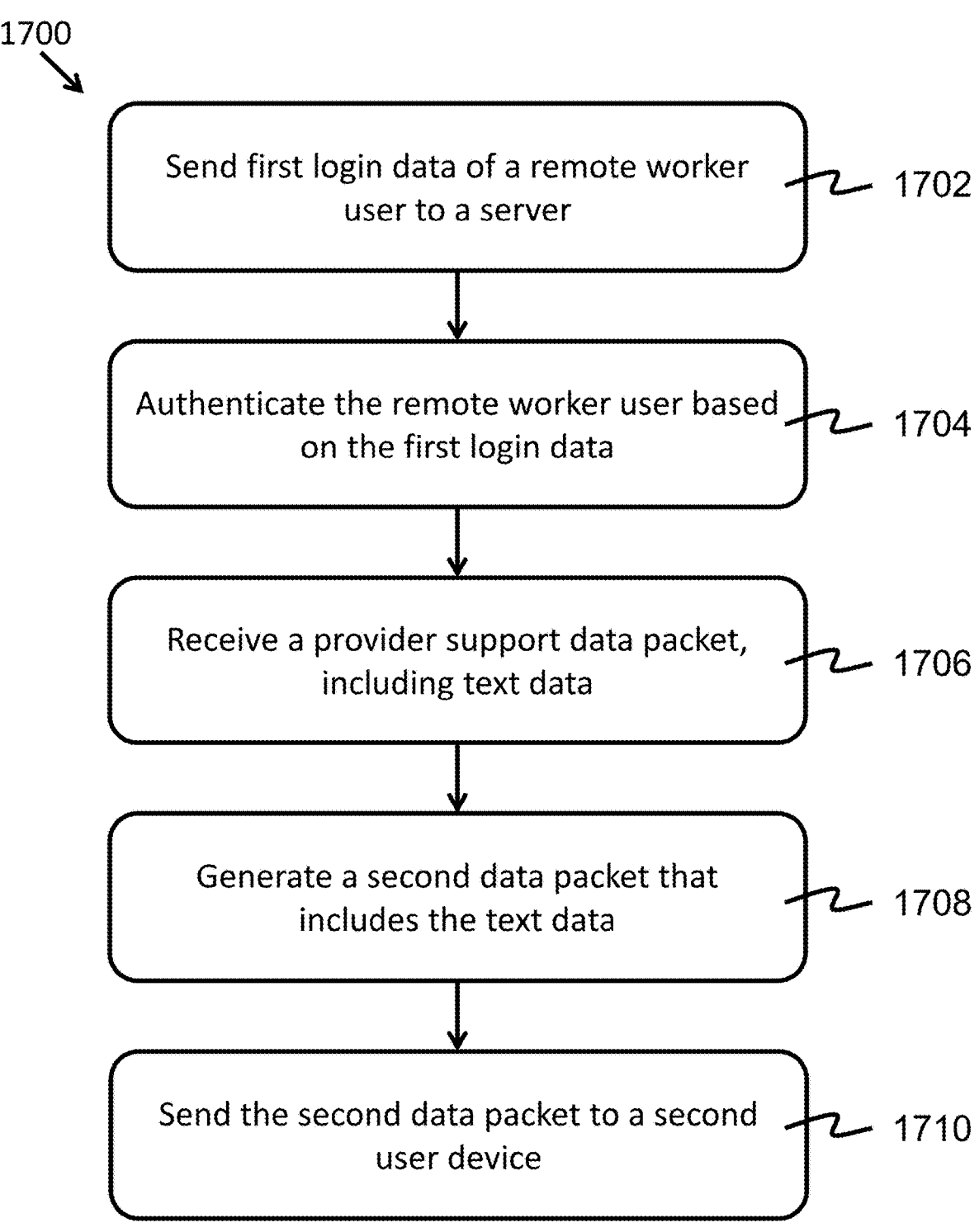
FIG. 17 is a flowchart illustrating one embodiment of a method of automating processes for remote work.

FIG. 17 depicts one embodiment of a method 1700. The method 1700 may include a method of automating processes for remote work. The method 1700 may include receiving 1702, at a server, first login data from a client software application executing on a first user device of a first remote worker user. The remote worker user may include a medical provider user. The method 1700 may include authenticating 1704 the first remote worker user based on the first login data. The method 1700 may include receiving 1706, from the client software application, a provider support data packet. The provider support data packet may include text data. The method 1700 may include generating 1708 a second data packet. The second data packet may include the text data. The method 1700 may include sending 1710 the second data packet to a second user device of a second remote worker user. The second remote worker user may include a medical provider user. Various details and further embodiments of the method 1700 are described above.

Figure 18:
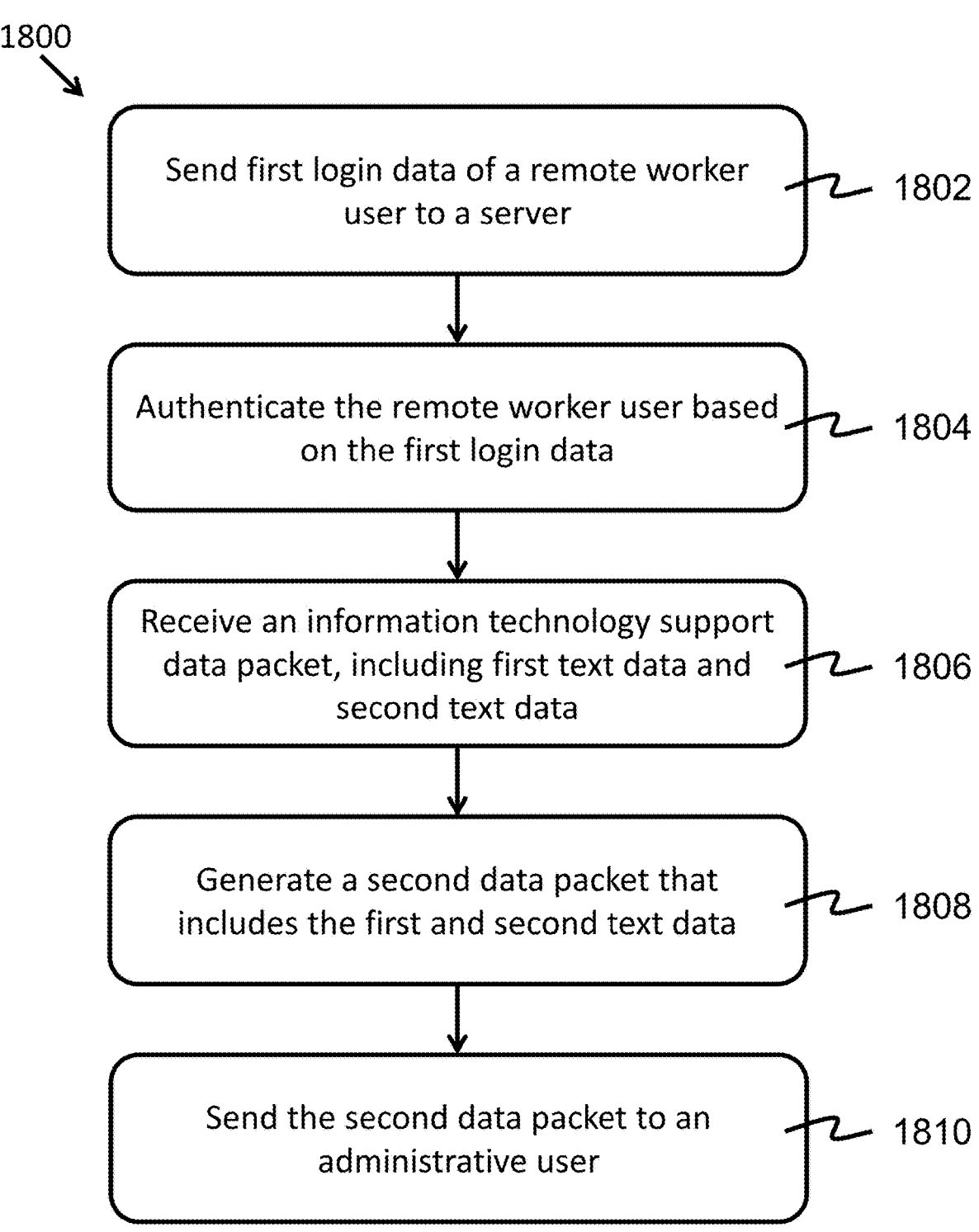
FIG. 18 is a flowchart illustrating one embodiment of a method of automating processes for remote work.

FIG. 18 depicts one embodiment of a method 1800. The method 1800 may include a method of automating processes for remote work. The method 1800 may include receiving 1802, at a server, first login data from a client software application executing on a first user device of a first remote worker user. The method 1800 may include authenticating 1804 the first remote worker user based on the first login data. The method 1800 may include receiving 1806, from the client software application, an information technology support data packet. The information technology support data packet may include a help ticket. The help ticket may include first text data indicating a subject of the help ticket, and second text data indicating a description of the help ticket. The method 1800 may include generating 1808 a second data packet. The second data packet may include the first text data and the second text data. The method 1800 may include sending 1810 the second data packet to an administrative user. Various details and further embodiments of the method 1800 are described above.

The systems and methods of the disclosure provide solutions to problems arising the context of remote computing. As mentioned above, in order to access multiple entities' systems **102(1)-(*n*), the remote worker must maintain different login information for each entity system 102. The systems and methods of the disclosure solve this problem by maintaining the login data for the remote worker user in a convenient and secure location. The systems and methods disclosed herein also automatically log the remote worker user into the different entity systems 102(1)-(*n*) using RPA processes (such as the RPA module 412 or RPA functionality of the software application 202 of the user device 104). Another remote computing problem is the remote worker user needing to maintain the different software applications used to access the entity systems 102(1)-(*n*). The systems and methods disclosed herein solve this problem by maintaining the software applications for the remote worker user (including maintaining different versions of the same software application) and providing desktop virtualization to the remote worker user to allow the remote worker user to remotely access the entity systems 102(1)-(*n*)**. Furthermore, another problem with remote computing is that the remote worker user must learn how to use the different entities' software application, which may vary greatly in their functionality. The systems and methods disclosed herein solve this problem by providing RPA functionality that automates several tasks, such as logging into the software application, creating a new account, or performing common tasks in the software applications.

The systems and method disclosed herein provide improvements to the functioning of computers. By maintaining the login information for the remote worker user in a secure location and transmitting the login information in a secure manner, the data security of the systems is increased. By using RPA functionality to automate several different tasks for the remote worker user, the speed and efficiency of the system is also increased.

The systems and methods disclosed herein use nonconventional and non-generic arrangements of computer components. For example, arranging a platform, such as the platform 204, between the user device 104 and the entity systems **102(1)-(*n*) is unconventional in the prior art (as shown in FIG. 1). The use of remote access module 402 to direct data between the user device 104 and the entity systems 102(1)-(*n*) is not found in prior systems. The account module 404, software module 406, and entity module 408 maintaining and coordinating data for the remote worker user of the user device 104 and the entity systems 102(1)-(*n*) is also not found in prior conventional systems. Additionally, the use of RPA processes (such as the RPA module 412) to automate several tasks that the remote worker user may perform when interacting with the entity systems 102(1)-(*n*)** is not found in conventional remote work systems.

Reference throughout this specification to "one embodiment," "an embodiment," "another embodiment," or similar language means that a particular feature, structure, or characteristic described in connection with the embodiment is included in at least one embodiment. Thus, appearances of the phrases "in one embodiment," "in an embodiment," "in some embodiments," and similar language throughout this specification may, but do not necessarily, all refer to the same embodiment, but mean "one or more but not necessarily all embodiments" unless expressly specified otherwise.

The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. As used herein, the term "a," "an," or "the" means "one or more" unless otherwise specified. The term "or" means "and/or" unless otherwise specified.

Multiple elements of the same or a similar type may be referred to as "Elements **102(1)-(*n*)" where n may include a number. Referring to one of the elements as "Element 102" refers to any single element of the Elements 102(1)-(*n*). Additionally, referring to different elements "First Elements 102(1)-(*n*)" and "Second Elements 104(1)-(*n*)" does not necessarily mean that there must be the same number of First Elements as Second Elements and is equivalent to "First Elements 102(1)-(*n*)" and "Second Elements (1)-(*m*)**" where m is a number that may be the same or may be a different number than n.

While the making and using of various embodiments of the present disclosure are discussed in detail herein, it should be appreciated that the present disclosure provides many applicable inventive concepts that are embodied in a wide variety of specific contexts. The specific embodiments discussed herein are merely illustrative of specific ways to make and use the disclosure and do not delimit the scope of the disclosure. Those of ordinary skill in the art will recognize numerous equivalents to the specific apparatuses, systems, and methods described herein. Such equivalents are considered to be within the scope of this disclosure and may be covered by the claims.

Furthermore, the described features, structures, or characteristics of the disclosure may be combined in any suitable manner in one or more embodiments. In the description contained herein, numerous specific details are provided, such as examples of programming, software, user selections, hardware, hardware circuits, hardware chips, or the like, to provide understanding of embodiments of the disclosure. One skilled in the relevant art will recognize, however, that the disclosure may be practiced without one or more of the specific details, or with other methods, components, materials, apparatuses, devices, systems, and so forth. In other instances, well-known structures, materials, or operations may not be shown or described in detail to avoid obscuring aspects of the disclosure.

These features and advantages of the embodiments will become more fully apparent from the description and appended claims, or may be learned by the practice of embodiments as set forth herein. As will be appreciated by one skilled in the art, aspects of the present disclosure may be embodied as an apparatus, system, method, computer program product, or the like. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present disclosure may take the form of a computer program product embodied in one or more computer-readable media having program code embodied thereon.

In some embodiments, a module may be implemented as a hardware circuit comprising custom (very large-scale integration) VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer-readable media.

In some embodiments, a module may include a smart contract hosted on a blockchain. The functionality of the smart contract may be executed by a node (or peer) of the blockchain network. One or more inputs to the smart contract may be read or detected from one or more transactions stored on or referenced by the blockchain. The smart contract may output data based on the execution of the smart contract as one or more transactions to the blockchain. A smart contract may implement one or more methods or algorithms described herein.

The computer program product may include a computer-readable storage medium (or media) having computer-readable program instructions thereon for causing a processor to carry out aspects of the present disclosure. The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium may include a portable computer diskette, a random access memory ("RAM"), a read-only memory ("ROM"), an erasable programmable read-only memory ("EPROM" or Flash memory), a static random access memory ("SRAM"), a hard disk drive ("HDD"), a solid state drive, a portable compact disc read-only memory ("CD-ROM"), a digital versatile disk ("DVD"), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry, in order to perform aspects of the present disclosure.

Aspects of the present disclosure are described herein with reference to flowchart illustrations or block diagrams of methods, apparatuses, systems, algorithms, or computer program products according to embodiments of the disclosure. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The schematic flow chart diagrams included herein are generally set forth as logical flow chart diagrams. As such, the depicted order and labeled steps are indicative of one embodiment of the presented method. Other steps and methods may be conceived that may be equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The schematic flowchart diagrams and/or schematic block diagrams in the Figures illustrate the architecture, functionality, and operation of possible implementations of apparatuses, systems, methods and computer program products according to various embodiments of the present disclosure. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Thus, although there have been described particular embodiments of the present disclosure of a new and useful systems and methods of automating processes for remote work, it is not intended that such references be construed as limitations upon the scope of this disclosure.

What is claimed is:

1. A non-transitory computer-readable storage medium having executable instructions stored thereon, wherein the executable instructions, when executed by a processor, are configured to:

receive, at a server, first login data from a client software application executing on a user device of a remote worker user;

authenticate the remote worker user based on the first login data;

send, to the client software application of the user device, data indicating a plurality of hospital entities and data indicating at least one software application associated with one or more hospital entities of the plurality of hospital entities;

receive, from the client software application, selection data for at least one hospital entity of the plurality of hospital entities selected by the remote worker user including a first hospital entity identifier corresponding to the at least one hospital entity of the plurality of hospital entities selected by the remote worker user;

retrieve, based on the first hospital entity identifier, hospital entity data including data for the at least one hospital entity selected by the remote worker user from a database in data communication with the server; and send, to the client software application, at least a portion of the hospital entity data;

receive, at the server, a clinical activity log data packet, wherein the clinical activity log data packet includes:

a second hospital entity identifier, data indicating an encounter type, data indicating an identity of a patient, and first text data;

generate a clinical activity log entry based on the clinical activity log data packet;

store the clinical activity log entry in the database in data communication with the server;

receive, at the server, at least one onboarding data packet; and generate at least one database entry in an entity user account database.

2. The non-transitory computer-readable storage medium of claim 1, wherein the at least one onboarding data packet comprises a first onboarding data packet and a second onboarding data packet.

3. The non-transitory computer-readable storage medium of claim 2, wherein the first onboarding data packet includes:

a first username, a first password, data indicating a selection of a first software application of one or more software applications, and data indicating a selection, by the remote worker user, of a first hospital entity of the plurality of hospital entities;

wherein the at least one database entry comprises a first database entry, wherein the first database entry includes:

data indicating the first hospital entity, data indicating the first software application,
the first username, and
the first password;
receive, at the server, command data from the client
software application, wherein the command data
includes data indicating to the server to launch a second
software application;
launch, on the server, the second software application; and
input, using a robotic process automation (RPA) process,
second login data of the remote worker user into the
second software application.

4. The non-transitory computer-readable storage medium
of claim 3, wherein the second onboarding data packet
includes:
a second username,
a second password,
data indicating a selection of a third software applica-
tion of one or more software applications, and
data indicating a selection, by the remote worker user,
of a second hospital entity of the plurality of hospital
entities, wherein the second hospital entity is differ-
ent from the first hospital entity;
wherein the at least one database entry comprises a
second database entry, wherein the second database
entry includes:
data indicating the second hospital entity,
data indicating the third software application,
the second username, and
the second password;
receive data, at the server, indicating a selection of the first
software application or the third software application;
launch the selected first software application or the third
software application; and
receive data, at the server, indicating a selection of the first
hospital entity or the second hospital entity from the
remote worker user;
input into the selected first software application or the
third software application, based on the selection of the
first hospital entity or the second hospital entity, the
first username and the first password or the second
username and the second password.

5. The non-transitory computer-readable storage medium
of claim 4, wherein the first software application and the
third software application are the same software application.

6. The non-transitory computer-readable storage medium
of claim 4, wherein at least one of:
the second username is different than the first username;
or
the second password is different than the first password.

7. The non-transitory computer-readable storage medium
of claim 1, wherein the hospital entity data comprises fourth
text data, and wherein the fourth text data includes:
a category; and
a corresponding value for the category.

8. The non-transitory computer-readable storage medium
of claim 7, wherein the category comprises at least one of:
a nursing station;
a call schedule;
information technology contact information;
handoff information; and
treatment information.

9. The non-transitory computer-readable storage medium
of claim 8, wherein the corresponding value includes a
hyperlink.

10. The non-transitory computer-readable storage
medium of claim 1, wherein the client software application
comprises at least one of a web browser and a mobile
application.

11. The non-transitory computer-readable storage
medium of claim 1, wherein:
the clinical activity log data packet includes an encrypted
data packet; and
the executable instructions being configured to receive the
clinical activity log data packet comprises decrypting
the clinical activity log data packet.

12. A computer-implemented method of presenting site
information to a remote worker user, comprising:
receiving, at a server, first login data from a client
software application executing on a first user device of
the remote worker user, wherein the remote worker
user includes a medical worker user;
authenticating the remote worker user based on the first
login data;
sending, to the client software application of the first user
device, data indicating a plurality of healthcare entities
and data indicating at least one software application
associated with one or more healthcare entities of the
plurality of healthcare entities;
receiving, from the client software application, selection
data for at least one healthcare entity of the plurality of
healthcare entities selected by the remote worker user
including a first healthcare entity identifier including
data that identifies a healthcare entity system corre-
sponding to the at least one healthcare entity of the
plurality of healthcare entities selected by the remote
worker user;
retrieving, based on the first healthcare entity identifier,
healthcare entity data including data for the at least one
healthcare entity selected by the remote worker user
from a database in data communication with the server
and first text data comprising a category and a corre-
sponding value for the category;
sending, to the client software application, at least a
portion of the healthcare entity data;
receiving, at the server, a clinical activity log data packet,
wherein the clinical activity log data packet includes:
a second healthcare entity identifier,
data indicating an encounter type,
data indicating an identity of a patient, and
second text data;
generating a clinical activity log entry based on the
clinical activity log data packet;
storing the clinical activity log entry in the database in
data communication with the server;
receiving, at the server, at least one onboarding data
packet; and
generating at least one database entry in an entity user
account database.

13. The computer-implemented method of claim 12,
wherein the at least one onboarding data packet comprises a
first onboarding data packet and a second onboarding data
packet.

14. The computer-implemented method of claim 13,
wherein the first onboarding data packet includes:
a first username,
a first password,
data indicating a selection of a first software application
of one or more software applications, and
data indicating a selection, by the remote worker user,
of a first healthcare entity of a plurality of healthcare
entities; and wherein the at least one database entry comprises a first database, wherein the first database entry includes:

data indicating the first healthcare entity, data indicating the first software application, the first username, and the first password receiving, at the server, command data from the client software application, wherein the command data includes data indicating to the server to launch a software application;

launching, on the server, the software application; and inputting, using a robotic process automation (RPA) process, second login data of the remote worker user into the software application.

15. The computer-implemented method of claim 14, further comprising:

receiving, at the server, a second onboarding data packet, wherein the second onboarding data packet includes:

a second username, a second password, data indicating a selection of a third software application of one or more software applications, and data indicating a selection of the second healthcare entity of a plurality of healthcare entities, wherein the second healthcare entity is different from the first healthcare entity; and presenting, via the client software application, the second username, the second password, the data indicating the selection of the third software application, and the data indicating the selection of the second healthcare entity;

wherein the at least one database entry comprises a second database entry, wherein the second database entry includes:

data indicating the second healthcare entity, data indicating the third software application, the second username, and the second password;

receiving data, at the server, indicating a selection of the first software application or the third software application;

launching the selected first software application or the third software application; and receiving data, at the server, indicating a selection of the first healthcare entity or the second healthcare entity from the remote worker user; and inputting into the selected first software application or the third software application, based on the selection of the first healthcare entity or the second healthcare entity, the first username and the first password or the second username and the second password.

16. The computer-implemented method of claim 12, wherein the category comprises at least one of:

frequently used contact information;

software application information;

medical facility technology information;

software application information; or medical facility technology information.

17. The computer-implemented method of claim 16, wherein the corresponding value includes a hyperlink.

18. The computer-implemented method of claim 12, further comprising:

retrieving a plurality of clinical activity log entries from the database, wherein the plurality of clinical activity log entries includes the clinical activity log entry; and generating a spreadsheet file based on the plurality of clinical activity log entries.

19. The computer-implemented method of claim 12, wherein the client software application comprises at least one of a web browser and a mobile application.

20. The computer-implemented method of claim 14, wherein launching, on the server, the software application, comprises:

launching, on the server, a virtual machine, wherein the virtual machine includes the software application installed on the virtual machine.

* * * * *